(12) United States Patent
Buettelmann et al.

(10) Patent No.: US 7,851,469 B2
(45) Date of Patent: Dec. 14, 2010

(54) ISOXAZOLE-IMIDAZOLE DERIVATIVES

(75) Inventors: Bernd Buettelmann, Palo Alto, CA (US); Roland Jakob-Roetne, Inzlingen (DE); Henner Knust, Rheinfelden (DE); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 361 days.

(21) Appl. No.: 12/139,535

(22) Filed: Jun. 16, 2008

(65) Prior Publication Data
US 2009/0005370 A1 Jan. 1, 2009

(30) Foreign Application Priority Data
Jun. 22, 2007 (EP) ................... 07110846

(51) Int. Cl.
| A61K 31/541 | (2006.01) |
| A61K 31/422 | (2006.01) |
| A61K 31/4439 | (2006.01) |
| A61K 31/506 | (2006.01) |
| C07D 261/06 | (2006.01) |
| C07D 241/10 | (2006.01) |
| C07D 239/24 | (2006.01) |
| C07D 213/02 | (2006.01) |

(52) U.S. Cl. .............. 514/228.8; 514/255.05; 514/256; 514/341; 514/378; 544/60; 544/405; 546/272.1; 548/247

(58) Field of Classification Search ........... None
See application file for complete search history.

(56) References Cited

U.S. PATENT DOCUMENTS

| 4,639,266 A | 1/1987 | Heubach et al. |
| 2003/0055085 A1 | 3/2003 | Wagener et al. |
| 2004/0006226 A1 | 1/2004 | Ladduwahetty et al. |
| 2004/0132755 A1* | 7/2004 | Ledeboer et al. ............ 514/275 |

FOREIGN PATENT DOCUMENTS

| DE | 3525205 | 3/1986 |
| GB | 2336589 | 10/1999 |
| WO | WO 01/29015 | 4/2001 |
| WO | WO 01/34603 | 5/2001 |
| WO | WO 02/50062 A2 | 6/2002 |
| WO | WO 02/81474 A1 | 10/2002 |
| WO | WO 03/004027 | 1/2003 |
| WO | WO 03/044017 | 5/2003 |
| WO | WO 2005/014553 | 2/2005 |
| WO | WO 2005/118568 | 12/2005 |
| WO | WO 2005/123672 A2 | 12/2005 |
| WO | WO 2006/044617 | 4/2006 |
| WO | WO 2006/069155 | 9/2006 |
| WO | WO 2007/074078 | 7/2007 |
| WO | WO 2007/074089 | 7/2007 |
| WO | WO 2007/082806 | 7/2007 |

OTHER PUBLICATIONS

McNamara et al., Psychobiology (1993), vol. 21, pp. 101-108.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Burke, et al., Journal of Natural Products, 1986, vol. 49, pp. 522-523.
Hamper et al., J. Agric. Food Chem. (1995), vol. 43, pp. 219-228.
Kumar, et al., Tetrahedron Letters, vol. 47, (2006), p. 1457-1460.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Austin et al., J. Org. Chem. vol. 46, pp. 2280-2286 (1981).
Schlosser et al., Eur. J. Org. Chem. vol. (24), p. 4181-4184 (2002).
Hüttel et al., Liebigs, Ann. Chem. vol. 593, pp. 200-207 (1955) (English translation).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Félix et al., J. Org. Chem. 1995, vol. 60 p. 3907-3909.

* cited by examiner

*Primary Examiner*—Kamal A Saeed
(74) *Attorney, Agent, or Firm*—George W. Johnston; Patricia S. Rocha-Tramaloni; Kimberly J. Prior

(57) ABSTRACT

The present invention is concerned isoxazole-imidazole derivatives having affinity and selectivity for GABA A α5 receptor binding site, their manufacture, pharmaceutical compositions containing them and their use for enhancing cognition or for the treatment of cognitive disorders like Alzheimer's disease. In particular, the present invention is concerned with aryl-isoxazol-4-yl-imidazole derivatives of formula I

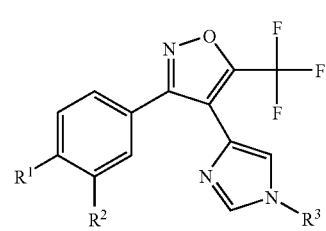

wherein $R^1$, $R^2$ and $R^3$ are as described in the specification.

15 Claims, No Drawings

ISOXAZOLE-IMIDAZOLE DERIVATIVES

PRIORITY TO RELATED APPLICATION(s)

This application claims the benefit of European Patent Application No. 07110846.8, filed Jun. 22, 2007, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology,* 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides isoxazole-imidazole derivatives having affinity and selectivity for GABA A α5 receptor binding site, their manufacture, pharmaceutical compositions containing them and methods of enhancing cognition or of treating cognitive disorders, such as Alzheimer's disease with them.

In particular, the present invention provides aryl-isoxazol-4-yl-imidazole derivatives of formula I

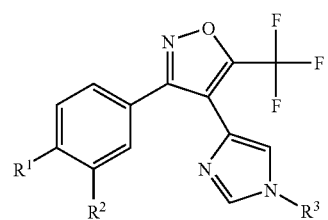

wherein
$R^1$ and $R^2$ are each independently hydrogen, halogen, or $C_{1-7}$-haloalkoxy;
$R^3$ is phenyl or 6-membered heteroaryl, each of which is optionally substituted by one or more
halogen,
$C_{1-7}$-alkyl, optionally substituted with halo, hydroxy or cyano,
$C_{1-7}$-alkoxy,
—$S(O)_m$—$C_{1-7}$-alkyl, wherein m is 0, 1 or 2,
cyano,
nitro,
—$C(O)R^a$, wherein $R^a$ is
  $C_{1-7}$-alkyl,
  $C_{1-7}$-alkoxy,
  hydroxy,
  —$(CH_2)_n$—$C_{3-7}$-cycloalkyl,
  —$(CH_2)_n$-(3- to 7-membered heterocycloalkyl), optionally substituted by $C_{1-4}$-alkyl, halo, hydroxy, or oxo,
  —$O(CH_2)_n$—$C_{3-7}$-cycloalkyl,
—$NC(O)C_{1-7}$-alkyl,
—$NC(O)OC_{1-7}$-alkyl,
—$C(O)NR^bR^c$, wherein $R^b$ and $R^c$ are independently
  hydrogen,
  $C_{1-7}$-alkyl,
  —$(CH_2)_p$-(3- to 7-membered heterocycloalkyl), optionally substituted by $C_{1-4}$-alkyl, halo, hydroxy, or oxo,
  —$(CH_2)_p$-(5- or 6-membered heteroaryl) or —$(CH_2)_r$-phenyl, each optionally substituted by halo, $C_{1-4}$-alkyl, $C_{1-7}$-haloalkyl, $C_{1-7}$-alkoxy, cyano or nitro,
  —$(CH_2)_q$—$C_{3-7}$-cycloalkyl,
  $C_{1-7}$-haloalkyl,
  $C_{1-7}$-alkynyl,
  or $R^b$ and $R^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more $C_{1-4}$-alkyl, halo, hydroxy, or oxo;
n is 0, 1, 2, 3 or 4;
p is 0, 1, 2, 3 or 4;
q is 0, 1, 2, 3 or 4; and
r is 0, 1, 2, 3 or 4;

or a pharmaceutically acceptable salt thereof.

The most preferred indication in accordance with the present invention is Alzheimer's disease.

DETAILED DESCRIPTION OF THE INVENTION

The following definitions of the general terms used in the present description apply irrespective of whether the terms in question appear alone or in combination.

As used herein, the term "alkyl" denotes a saturated straight- or branched-chain hydrocarbon group containing from 1 to 7 carbon atoms, for example, methyl, ethyl, propyl, isopropyl, n-butyl, iso-butyl, sec-butyl, tert-butyl and the like. Preferred alkyl groups are groups with 1 to 4 carbon atoms.

The terms "halo-$C_{1-7}$-alkyl", "$C_{1-7}$-haloalkyl" and "$C_{1-7}$-alkyl optionally substituted with halo" each denotes a $C_{1-7}$-alkyl group as defined above wherein at least one of the hydrogen atoms of the alkyl group is replaced by a halogen atom, preferably fluoro or chloro, most preferably fluoro. Examples of halo-$C_{1-7}$-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below. Among the preferred halo-$C_{1-7}$-alkyl groups are difluoro- or trifluoro-methyl or -ethyl.

The terms "hydroxy-$C_{1-7}$-alkyl", "$C_{1-7}$-hydroxyalkyl" and "$C_{1-7}$-alkyl optionally substituted with hydroxy" each denotes a $C_{1-7}$-alkyl group as defined above wherein at least one of the hydrogen atoms of the alkyl group is replaced by a hydroxy group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one hydroxy group, as well as those groups specifically illustrated by the examples herein below.

The terms "cyano-$C_{1-7}$-alkyl", "$C_{1-7}$-cyanoalkyl" and "$C_{1-7}$-alkyl optionally substituted with cyano" each denotes a $C_{1-7}$-alkyl group as defined above wherein at least one of the hydrogen atoms of the alkyl group is replaced by a cyano group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more cyano group(s), preferably by one, two or three, and more preferably by one cyano group, as well as those groups specifically illustrated by the examples herein below.

The term "alkoxy" denotes a group —O—R' wherein R' is alkyl as defined above.

The term "halo" or "halogen" denotes chloro, iodo, fluoro and bromo.

The terms "$C_{1-7}$-haloalkoxy" and "halo-$C_{1-7}$-alkoxy" each denotes a $C_{1-7}$-alkoxy group as defined above wherein at least one of the hydrogen atoms of the alkoxy group is replaced by a halogen atom, preferably fluoro or chloro, most preferably fluoro. Examples of halo-$C_{1-7}$-alkoxy include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro atoms, as well as those groups specifically illustrated by the examples herein below. Among the preferred halo-$C_{1-7}$-alkoxy groups are difluoro- or trifluoro-methoxy or -ethoxy substituted as described above, preferably —$OCF_3$.

The term "aromatic" means the presence of an electron sextet in a ring, according to Hückel's rule.

The term "cycloalkyl" refers to a monovalent saturated cyclic hydrocarbon radical of 3 to 7 ring carbon atoms, preferably 3 to 6 carbon atoms, such as cyclopropyl, cyclopentyl, or cyclohexyl. Even more preferred is cyclopropyl.

The term "heterocycloalkyl" refers to a monovalent 3 to 7 membered saturated ring containing one, two or three ring heteroatoms selected from N, O and S. One or two ring heteroatoms are preferred. Preferred are 5 to 6 membered heterocycloalkyl, even more preferred are 6-membered heterocycloalkyl rings, each containing one or two ring heteroatoms selected from N, O and S. Examples for heterocycloalkyl moieties are tetrahydrofuranyl, tetrahydropyranyl, pyrrolidinyl, morpholinyl, thiomorpholinyl, piperidinyl, or piperazinyl. Preferred heterocycloalkyl moieties are tetrahydropyran-4-yl, morpholinyl, and thiomorpholinyl. Heterocycloalkyl is optionally substituted as described herein. As an example, thiomorpholinyl-1,1-dioxide may be mentioned.

The term "heteroaryl" refers to a monovalent aromatic 5- or 6-membered monocyclic ring containing one, two, or three ring heteroatoms selected from N, O, and S, the remaining ring atoms being C. Preferably, the 5- or 6-membered heteroaryl ring contains one or two ring heteroatoms. 6-membered heteroaryl are preferred. Examples for heteroaryl moieties include but are not limited to pyridinyl, pyrimidinyl, or pyrazinyl.

The term "oxo" when referring to substituents on heterocycloalkyl means that an oxygen atom is attached to the heterocycloalkyl ring. Thereby, the "oxo" may either replace two hydrogen atoms on a carbon atom, or it may simply be attached to sulfur, so that the sulfur exists in oxidized form, i.e. bearing one or two oxygens.

When indicating the number of substituents, the term "one or more" means from one substituent to the highest possible number of substitution, i.e. replacement of one hydrogen up to replacement of all hydrogens by substituents. Thereby, one, two or three substituents are preferred. Even more preferred are one or two substituents or one substituent.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In general, the nomenclature used in this Application is based on AUTONOM™ v.4.0, a Beilstein Institute computerized system for the generation of IUPAC systematic nomenclature.

In detail, the present invention provides compounds of the general formula (I)

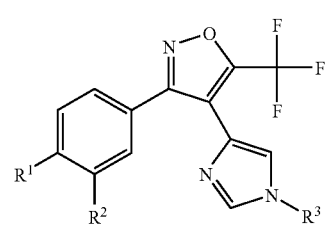

I wherein

R$^1$ and R$^2$ are each independently hydrogen, halogen, or C$_{1-7}$-haloalkoxy;

R$^3$ is phenyl or 5- or 6-membered heteroaryl, each of which is optionally substituted by one or more
- halogen,
- C$_{1-7}$-alkyl, optionally substituted with halo, hydroxy or cyano,
- C$_{1-7}$-alkoxy,
- —S(O)$_m$—C$_{1-7}$-alkyl, wherein m is 0, 1 or 2,
- cyano,
- nitro,
- —C(O)R$^a$, wherein R$^a$ is
  - C$_{1-7}$-alkyl,
  - C$_{1-7}$-alkoxy,
  - hydroxy,
  - —(CH$_2$)$_n$—C$_{3-7}$-cycloalkyl,
  - —(CH$_2$)$_n$-(3- to 7-membered heterocycloalkyl), optionally substituted by C$_{1-4}$-alkyl, halo, hydroxy, or oxo,
  - —O—(CH$_2$)$_n$—C$_{3-7}$-cycloalkyl,
- —NC(O)C$_{1-7}$-alkyl,
- —NC(O)OC$_{1-7}$-alkyl,
- —C(O)NR$^b$R$^c$, wherein R$^b$ and R$^c$ are independently
  - hydrogen,
  - C$_{1-7}$-alkyl,
  - —(CH$_2$)$_p$-(3- to 7-membered heterocycloalkyl), optionally substituted by C$_{1-4}$-alkyl, halo, hydroxy, or oxo,
  - —(CH$_2$)$_p$-(5- or 6-membered heteroaryl) or —(CH$_2$)$_r$-phenyl, each optionally substituted by halo, C$_{1-4}$-alkyl, C$_{1-7}$-haloalkyl, C$_{1-7}$-alkoxy, cyano or nitro,
  - —(CH$_2$)$_q$—C$_{3-7}$-cycloalkyl,
  - C$_{1-7}$-haloalkyl,
  - C$_{1-7}$-alkynyl,
  - or R$^b$ and R$^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more C$_{1-4}$-alkyl, halo, hydroxy, or oxo;

n is 0, 1, 2, 3 or 4;
p is 0, 1, 2, 3 or 4;
q is 0, 1, 2, 3 or 4; and
r is 0, 1, 2, 3 or 4;

or a pharmaceutically acceptable salt thereof.

The compounds of formula I can contain asymmetric carbon atoms. Accordingly, the present invention includes all stereoisomeric forms of the compounds of formula I, including each of the individual enantiomers and mixtures thereof, i.e. their individual optical isomers and mixtures thereof.

The variables p and q are preferably 0 or 1, more preferable p is 0 and q is 1 or 0.

The terms —(CH$_2$)$_n$—C$_{3-7}$-cycloalkyl and —(CH$_2$)$_q$—C$_{3-7}$-cycloalkyl mean that a C$_{3-7}$-cycloalkyl moiety is attached via a —(CH$_2$)$_n$— or —(CH$_2$)$_q$-linker, wherein n and q are 0, 1, 2, 3, or 4.

The terms —(CH$_2$)$_n$-(3- to 7-membered heterocycloalkyl) and —(CH$_2$)$_p$-(3- to 7-membered heterocycloalkyl) mean that a 3- to 7-membered heterocycloalkyl ring is attached via a —(CH$_2$)$_n$— or —(CH$_2$)$_p$-linker, wherein n and p are 0, 1, 2, 3, or 4. In case —(CH$_2$)$_n$-(3- to 7-membered heterocycloalkyl) and —(CH$_2$)$_p$-(3- to 7-membered heterocycloalkyl) are indicated to be optionally substituted by C$_{1-4}$-alkyl, halo, hydroxy, or oxo, this means that the optional substituents are attached to the 3- to 7-membered heterocycloalkyl ring. The number of optional substituents is hereby one, two or three, preferably one or two.

The term —(CH$_2$)$_p$-(5- or 6-membered heteroaryl) means that a 5- or 6-membered heteroaryl moiety is attached via a —(CH$_2$)$_p$-linker, wherein p is 0, 1, 2, 3 or 4. In case —(CH$_2$)$_p$-(5- or 6-membered heteroaryl) are indicated to be optionally substituted by halo, C$_{1-4}$-alkyl, C$_{1-7}$-haloalkyl, C$_{1-7}$-alkoxy, cyano or nitro, this means that the optional substituents are attached to the 5- or 6-membered heteroaryl ring. The number of optional substituents is hereby one, two or three, preferably one or two.

In all embodiments, the attachment point of the 3- to 7-membered heterocycloalkyl is preferably a carbon atom for p or n being 0, and a carbon or nitrogen atom for p or n being >0, i.e. p or n being 1, 2, 3, or 4.

In certain embodiments, R$^1$ and R$^2$ are as described above, namely each independently hydrogen, halogen, or C$_{1-7}$-haloalkoxy.

In further embodiments, R$^1$ and R$^2$ are each independently hydrogen, halogen or OCF$_3$. In preferred embodiments, R$^1$ and R$^2$ are hydrogen or halogen. In further embodiments, R$^1$ is hydrogen, fluoro or chloro, and R$^2$ is hydrogen or fluoro.

R$^3$ is phenyl or 6-membered heteroaryl, optionally substituted as described herein. Preferably, R$^3$ is phenyl, pyridinyl, pyrimidinyl, or pyrazinyl, for instance phenyl, pyrimidin-2-yl, pyridine-2-yl, or pyrazin-2-yl, all of them optionally substituted as described herein.

The aromatic ring of R$^3$ is optionally substituted by one or more substituents, preferred are one, two or three optional substituents, more preferred are one or two optional substituents or one optional substituent. In cases of one optional substituent on phenyl or 6-membered heteroaryl, substitution at the para-position is preferred.

In certain embodiments, the optional substituents for the aromatic ring of R$^3$ are as described above. Preferable optional substituents are
- halogen,
- C$_{1-7}$-alkyl, optionally substituted with halo, hydroxy or cyano,
- C$_{1-7}$-alkoxy,
- cyano,
- nitro,
- —C(O)R$^a$, wherein R$^a$ is
  - C$_{1-7}$-alkyl,
  - C$_{1-7}$-alkoxy,
  - hydroxy,
- —C(O)NR$^b$R$^c$, wherein R$^b$ and R$^c$ are independently
  - hydrogen,
  - 3- to 7-membered heterocycloalkyl, optionally substituted by C$_{1-4}$-alkyl, halo, hydroxy, or oxo,
  - —(CH$_2$)$_q$—C$_{3-7}$-cycloalkyl, wherein q is 0, 1, 2, 3 or 4, preferably 0 or 1,
  - C$_{1-7}$-haloalkyl,
  - or R$^b$ and R$^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more C$_{1-4}$-alkyl, halo, hydroxy, or oxo.

An example for a 3- to 7-membered heterocycloalkyl residue is tetrahydropyran-4-yl.

Examples for a 5- to 7-membered heterocycloalkyl built from R$^b$ and R$^c$ including the nitrogen to which they are attached are morpholinyl, thiomorpholinyl, and thiomorpholinyl-1,1-dioxide.

Preferred examples with $R^3$ being optionally substituted phenyl are 3-phenyl-4-(1-phenyl-1H-imidazol-4-yl)-5-trifluoromethyl-isoxazole,
4-[1-(4-fluoro-phenyl)-1H-imidazol-4-yl]-3-phenyl-5-trifluoromethyl-isoxazole,
1-{4-[4-(3-phenyl-5-trifluoromethyl-isoxazol-4-yl)-imidazol-1-yl]-phenyl}-ethanone,
3-phenyl-5-trifluoromethyl-4-[1-(4-trifluoromethyl-phenyl)-1H-imidazol-4-yl]-isoxazole,
4-[4-(3-phenyl-5-trifluoromethyl-isoxazol-4-yl)-imidazol-1-yl]-benzonitrile,
4-[4-(3-phenyl-5-trifluoromethyl-isoxazol-4-yl)-imidazol-1-yl]-benzoic acid methyl ester,
4-[1-(4-nitro-phenyl)-1H-imidazol-4-yl]-3-phenyl-5-trifluoromethyl-isoxazole,
3-phenyl-4-(1-p-tolyl-1H-imidazol-4-yl)-5-trifluoromethyl-isoxazole,
4-[1-(4-methoxy-phenyl)-1H-imidazol-4-yl]-3-phenyl-5-trifluoromethyl-isoxazole,
N-cyclopropylmethyl-4-[4-(3-phenyl-5-trifluoromethyl-isoxazol-4-yl)-imidazol-1-yl]-benzamide,
4-[4-(3-phenyl-5-trifluoromethyl-isoxazol-4-yl)-imidazol-1-yl]-N-(2,2,2-trifluoro-ethyl)-benzamide,
N-cyclopropyl-4-[4-(3-phenyl-5-trifluoromethyl-isoxazol-4-yl)-imidazol-1-yl]-benzamide,
4-[4-(3-phenyl-5-trifluoromethyl-isoxazol-4-yl)-imidazol-1-yl]-N-(tetrahydro-pyran-4-yl)-benzamide,
morpholin-4-yl-{4-[4-(3-phenyl-5-trifluoromethyl-isoxazol-4-yl)-imidazol-1-yl]-phenyl}-methanone,
{4-[4-(3-phenyl-5-trifluoromethyl-isoxazol-4-yl)-imidazol-1-yl]-phenyl}-thiomorpholin-4-yl-methanone,
1-(4-{4-[3-(4-fluoro-phenyl)-5-trifluoromethyl-isoxazol-4-yl]-imidazol-1-yl}-phenyl)-ethanone,
3-(4-fluoro-phenyl)-5-trifluoromethyl-4-[1-(4-trifluoromethyl-phenyl)-1H-imidazol-4-yl]-isoxazole,
4-{4-[3-(4-fluoro-phenyl)-5-trifluoromethyl-isoxazol-4-yl]-imidazol-1-yl}-benzonitrile,
4-{4-[3-(4-fluoro-phenyl)-5-trifluoromethyl-isoxazol-4-yl]-imidazol-1-yl}-benzoic acid methyl ester,
4-{4-[3-(4-fluoro-phenyl)-5-trifluoromethyl-isoxazol-4-yl]-imidazol-1-yl}-benzoic acid,
2-(4-{4-[3-(4-fluoro-phenyl)-5-trifluoromethyl-isoxazol-4-yl]-imidazol-1-yl}-phenyl)-propan-2-ol,
3-(4-fluoro-phenyl)-4-[1-(4-nitro-phenyl)-1H-imidazol-4-yl]-5-trifluoromethyl-isoxazole,
4-{4-[3-(4-fluoro-phenyl)-5-trifluoromethyl-isoxazol-4-yl]-imidazol-1-yl}-benzamide,
N-cyclopropylmethyl-4-{4-[3-(4-fluoro-phenyl)-5-trifluoromethyl-isoxazol-4-yl]-imidazol-1-yl}-benzamide,
4-{4-[3-(4-fluoro-phenyl)-5-trifluoromethyl-isoxazol-4-yl]-imidazol-1-yl}-N-(2,2,2-trifluoro-ethyl)-benzamide,
N-cyclopropyl-4-{4-[3-(4-fluoro-phenyl)-5-trifluoromethyl-isoxazol-4-yl]-imidazol-1-yl}-benzamide,
(1,1-dioxo-1λ6-thiomorpholin-4-yl)-(4-{4-[3-(4-fluoro-phenyl)-5-trifluoromethyl-isoxazol-4-yl]-imidazol-1-yl}-phenyl)-methanone,
1-(4-{4-[3-(4-chloro-phenyl)-5-trifluoromethyl-isoxazol-4-yl]-imidazol-1-yl}-phenyl)-ethanone,
3-(4-chloro-phenyl)-5-trifluoromethyl-4-[1-(4-trifluoromethyl-phenyl)-1H-imidazol-4-yl]-isoxazole,
4-{4-[3-(4-chloro-phenyl)-5-trifluoromethyl-isoxazol-4-yl]-imidazol-1-yl}-benzonitrile, and
3-(4-chloro-phenyl)-4-[1-(4-nitro-phenyl)-1H-imidazol-4-yl]-5-trifluoromethyl-isoxazole.

Preferred examples with $R^3$ being optionally substituted pyridinyl are

2-[4-(3-phenyl-5-trifluoromethyl-isoxazol-4-yl)-imidazol-1-yl]-5-trifluoromethyl-pyridine,
6-[4-(3-phenyl-5-trifluoromethyl-isoxazol-4-yl)-imidazol-1-yl]-nicotinic acid methyl ester,
N-cyclopropylmethyl-6-[4-(3-phenyl-5-trifluoromethyl-isoxazol-4-yl)-imidazol-1-yl]-nicotinamide,
6-[4-(3-phenyl-5-trifluoromethyl-isoxazol-4-yl)-imidazol-1-yl]-N-(2,2,2-trifluoro-ethyl)-nicotinamide,
N-cyclopropyl-6-[4-(3-phenyl-5-trifluoromethyl-isoxazol-4-yl)-imidazol-1-yl]-nicotinamide,
6-[4-(3-phenyl-5-trifluoromethyl-isoxazol-4-yl)-imidazol-1-yl]-N-(tetrahydro-pyran-4-yl)-nicotinamide,
morpholin-4-yl-{6-[4-(3-phenyl-5-trifluoromethyl-isoxazol-4-yl)-imidazol-1-yl]-pyridin-3-yl}-methanone,
{6-[4-(3-phenyl-5-trifluoromethyl-isoxazol-4-yl)-imidazol-1-yl]-pyridin-3-yl}-thiomorpholin-4-yl-methanone,
1-(6-{4-[3-(4-fluoro-phenyl)-5-trifluoromethyl-isoxazol-4-yl]-imidazol-1-yl}-pyridin-3-yl)-ethanone,
6-{4-[3-(4-fluoro-phenyl)-5-trifluoromethyl-isoxazol-4-yl]-imidazol-1-yl}-nicotinonitrile,
N-cyclopropylmethyl-6-{4-[3-(4-fluoro-phenyl)-5-trifluoromethyl-isoxazol-4-yl]-imidazol-1-yl}-nicotinamide,
6-{4-[3-(4-fluoro-phenyl)-5-trifluoromethyl-isoxazol-4-yl]-imidazol-1-yl}-N-(2,2,2-trifluoro-ethyl)-nicotinamide,
N-cyclopropyl-6-{4-[3-(4-fluoro-phenyl)-5-trifluoromethyl-isoxazol-4-yl]-imidazol-1-yl}-nicotinamide,
6-{4-[3-(4-fluoro-phenyl)-5-trifluoromethyl-isoxazol-4-yl]-imidazol-1-yl}-N-(tetrahydro-pyran-4-yl)-nicotinamide,
(1,1-dioxo-1λ6-thiomorpholin-4-yl)-(6-{4-[3-(4-fluoro-phenyl)-5-trifluoromethyl-isoxazol-4-yl]-imidazol-1-yl}-pyridin-3-yl)-methanone,
2-(6-{4-[3-(4-fluoro-phenyl)-5-trifluoromethyl-isoxazol-4-yl]-imidazol-1-yl}-pyridin-3-yl)-propan-2-ol,
6-{4-[3-(4-chloro-phenyl)-5-trifluoromethyl-isoxazol-4-yl]-imidazol-1-yl}-N-cyclopropylmethyl-nicotinamide,
6-{4-[3-(4-chloro-phenyl)-5-trifluoromethyl-isoxazol-4-yl]-imidazol-1-yl}-N-(2,2,2-trifluoro-ethyl)-nicotinamide,
6-{4-[3-(4-chloro-phenyl)-5-trifluoromethyl-isoxazol-4-yl]-imidazol-1-yl}-N-cyclopropyl-nicotinamide,
6-{4-[3-(4-chloro-phenyl)-5-trifluoromethyl-isoxazol-4-yl]-imidazol-1-yl}-N-(tetrahydro-pyran-4-yl)-nicotinamide,
(6-{4-[3-(4-chloro-phenyl)-5-trifluoromethyl-isoxazol-4-yl]-imidazol-1-yl}-pyridin-3-yl)-(1,1-dioxo-1λ6-thiomorpholin-4-yl)-methanone, and
N-cyclopropyl-6-{4-[3-(3-fluoro-phenyl)-5-trifluoromethyl-isoxazol-4-yl]-imidazol-1-yl}-nicotinamide.

A preferred example with $R^3$ being optionally substituted pyrazinyl is

5-[4-(3-phenyl-5-trifluoromethyl-isoxazol-4-yl)-imidazol-1-yl]-pyrazine-2-carboxylic acid cyclopropylamide.

A preferred example with $R^3$ being optionally substituted pyrimidinyl is

2-[4-(3-phenyl-5-trifluoromethyl-isoxazol-4-yl)-imidazol-1-yl]-pyrimidine.

In a certain embodiment of the invention, compounds of formula I are provided

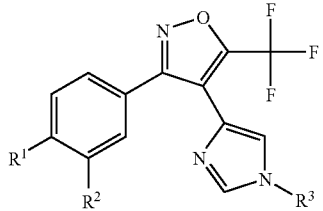

I wherein
$R^1$ and $R^2$ are each independently hydrogen, or halogen;
$R^3$ is phenyl or 6-membered heteroaryl, each of which is optionally substituted by one or more
halogen,
$C_{1-7}$-alkyl, optionally substituted with halo, hydroxy or cyano,
$C_{1-7}$-alkoxy,
cyano,
nitro,
—C(O)$R^a$, wherein $R^a$ is
$C_{1-7}$-alkyl,
$C_{1-7}$-alkoxy,
hydroxy,
—C(O)$NR^bR^c$, wherein $R^b$ and $R^c$ are independently
hydrogen,
—(CH$_2$)$_p$-(3- to 7-membered heterocycloalkyl), optionally substituted by $C_{1-4}$-alkyl, halo, hydroxy, or oxo,
—(CH$_2$)$_q$—C$_{3-7}$-cycloalkyl,
$C_{1-7}$-haloalkyl,
or $R^b$ and $R^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more $C_{1-4}$-alkyl, halo, hydroxy, or oxo;
p is 0; and
q is 0, or 1;
or a pharmaceutically acceptable salt thereof.

The present compounds of formula I and their pharmaceutically acceptable salts can be prepared by a process comprising the steps of:

a) reacting a compound of formula II:

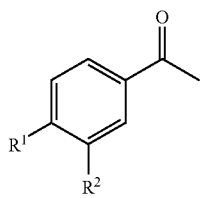

II with ethyl trifluoroacetate in a suitable solvent, such as tert-butylmethylether, in the presence of a base, such as sodium methoxide, to give a compound of formula III:

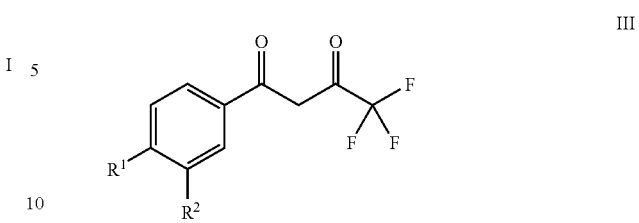

III b) reacting the compound of formula III with hydroxylamine hydrochloride in the presence of a suitable base, such as sodium hydroxide, in a suitable solvent, such as ethanol, to give a compound of formula IV:

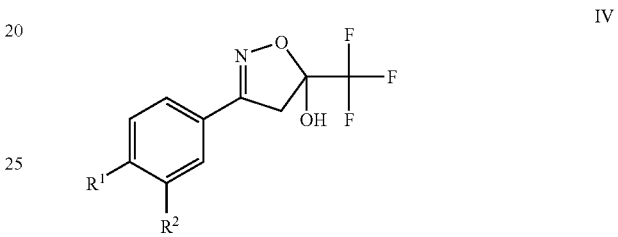

IV c) reacting the compound of formula IV with trifluoroacetic acid, to give a compound of formula V:

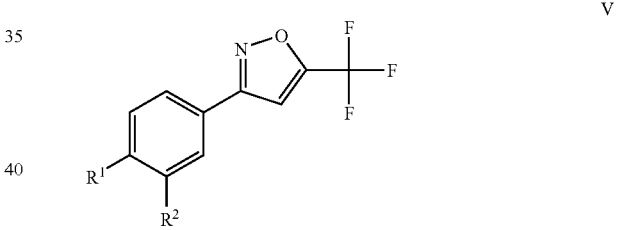

V d) reacting the compound of formula V with a base, such as BuLi and 2,2,6,6-tetramethylpiperidine in a suitable solvent such as THF followed by carbon dioxide, to give a compound of formula VI:

VI e) reacting the compound of formula VI with thionyl chloride in a suitable solvent such as toluene in the presence of a catalytic amount of DMF at elevated temperatures, for example 80° C., to give a compound of formula VI:

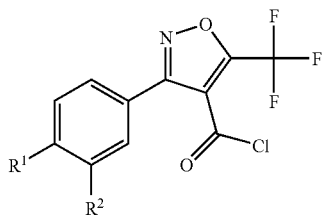

VII f) reacting the compound of formula VII with bis(trimethylsilyl) malonate in the presence of magnesium chloride in a suitable solvent, such as acetonitrile, in the presence of a base such as triethylamine, followed be heating in the presence of acid, such as HCl, to give a compound of formula VIII:

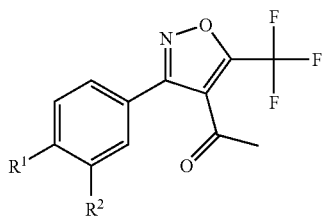

VIII g) or alternatively, by reacting the compound of formula V with BuLi in a suitable solvent, such as dimethoxyethane at reduced temperature (−35 to −78° C.) followed by addition of a suspension of copper(I) cyanide and lithium chloride in a suitable solvent, such as THF, followed by the addition of acetyl chloride, to give a compound of formula VIII:

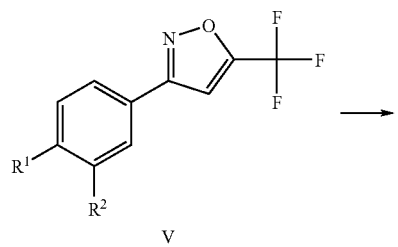

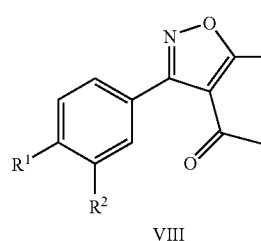

VIII h) reacting the compound of formula VIII with bromine in acetic acid in a suitable solvent, such as chloroform, at elevated temperatures, such as 50° C., to give a compound of formula IX:

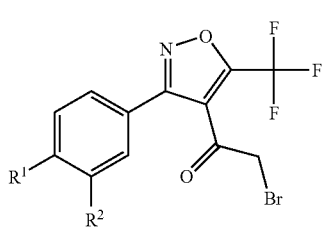

IX i) reacting the compound of formula IX with formamide and water at elevated temperatures, such as 80° C. or 140° C., to give a compound of formula X:

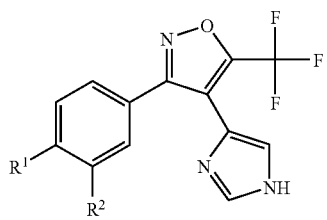

X j) reacting the compound of formula IX with DMSO and water, to give a compound of formula XI which is then reacted with 2-hydroxy-2-methoxyacetic acid methyl ester and ammonium acetate in a suitable solvent, such as acetonitrile and water, give a compound of formula XII which is then reacted with a suitable base, such as lithium hydroxide monohydrate, in a suitable solvent, such as THF and water, to give a compound of formula X:

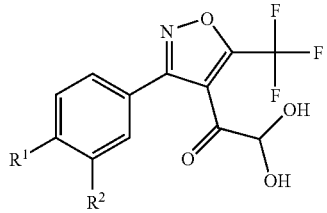

XI

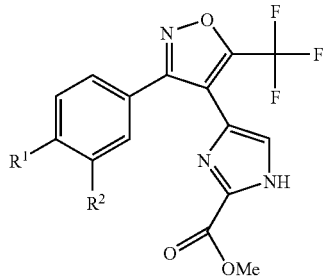

XII

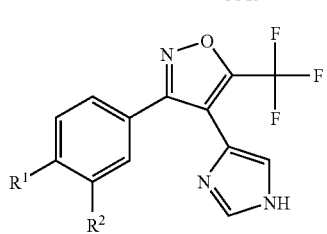

X k) reacting the compound of formula X with a range of electrophiles with further derivatisation shown in Schemes 1-8, to give a compound of formula I:

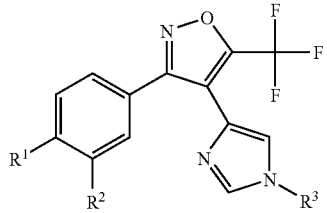

I wherein $R^1$ to $R^3$ are as described for formula I hereinabove, and, if desired, converting a compound of formula I into a pharmaceutically acceptable salt.

The following schemes describe the processes for preparation of compounds of formula I in more detail.
In accordance with Scheme 1, compounds of formula I can be prepared following standards methods.
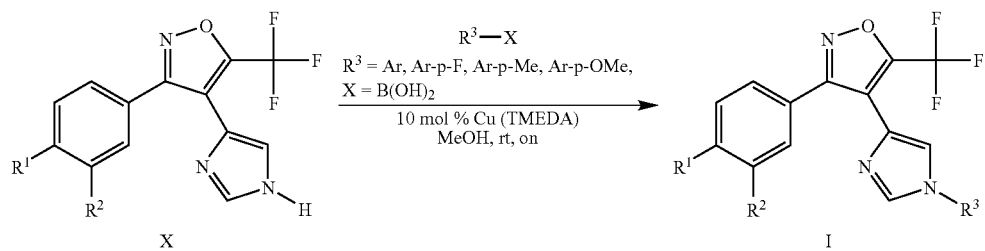
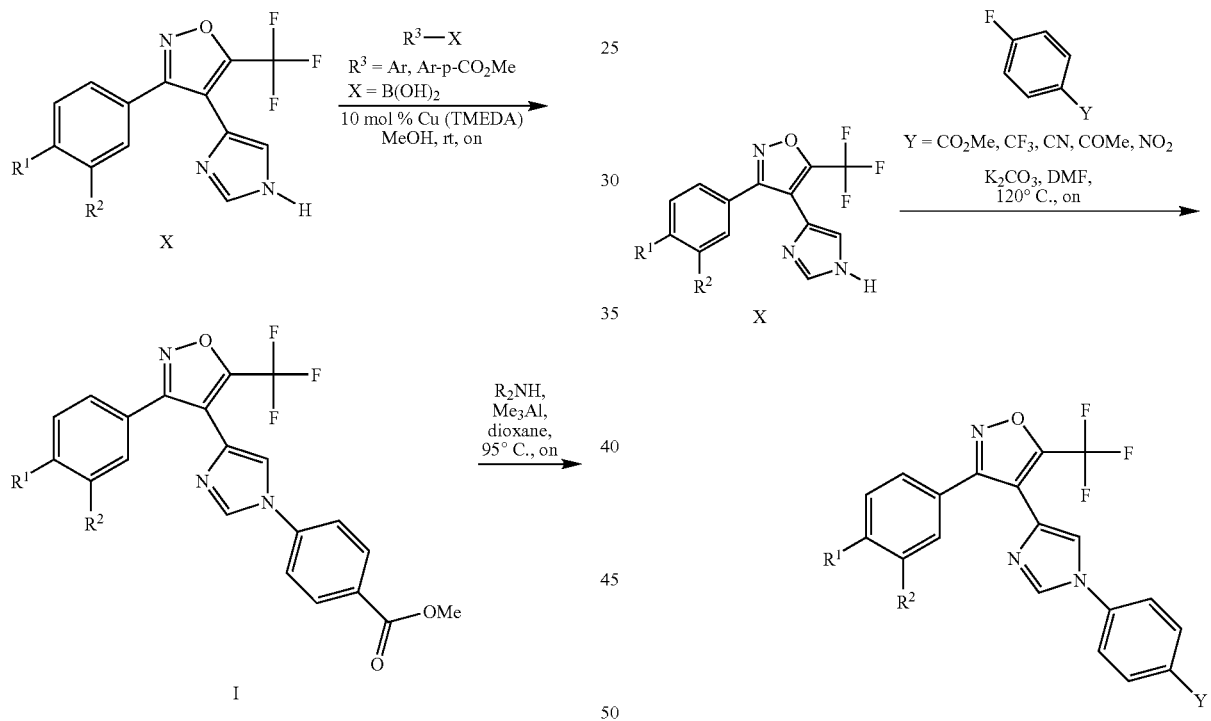
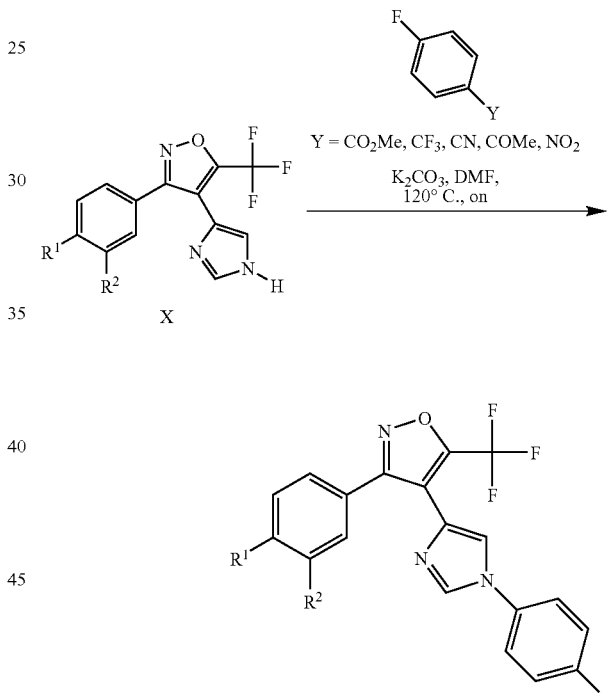
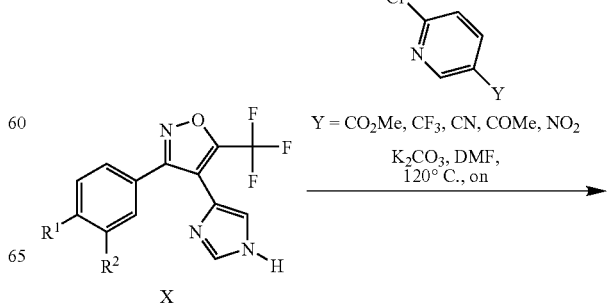

-continued
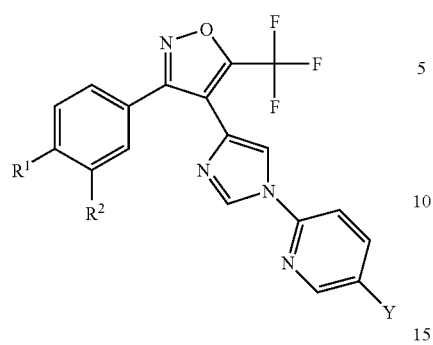
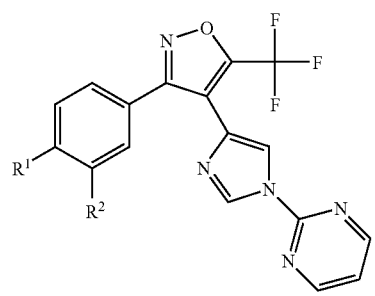
Scheme 5
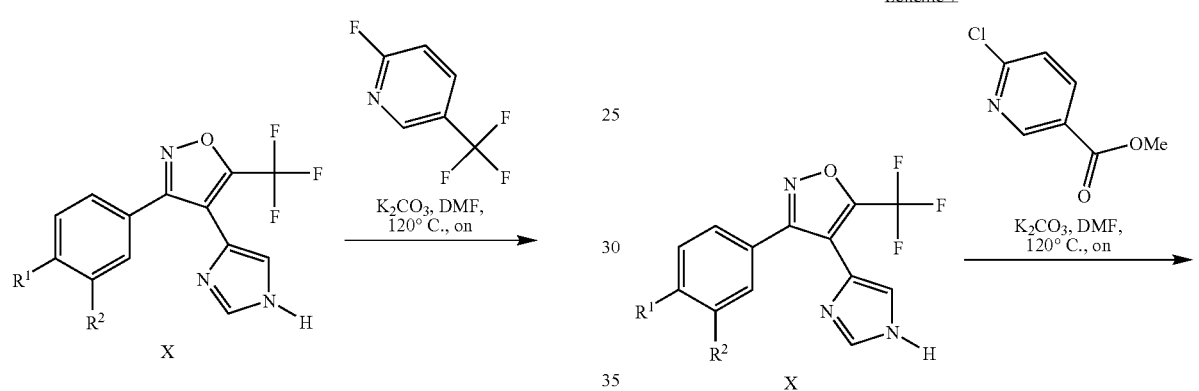
Scheme 7
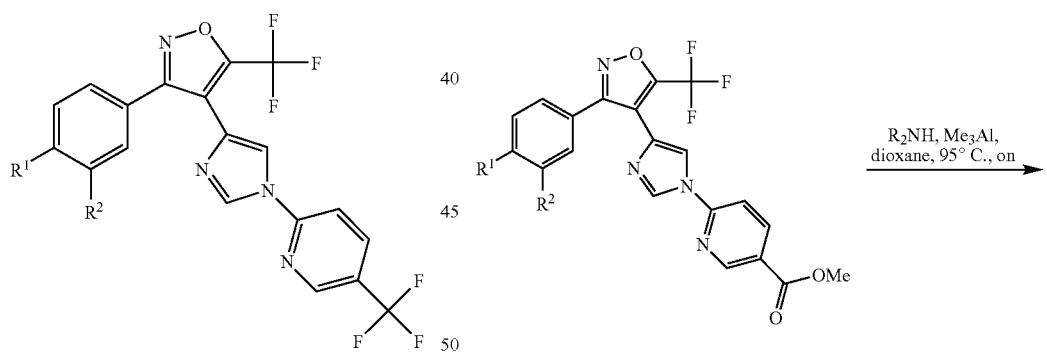
Scheme 6
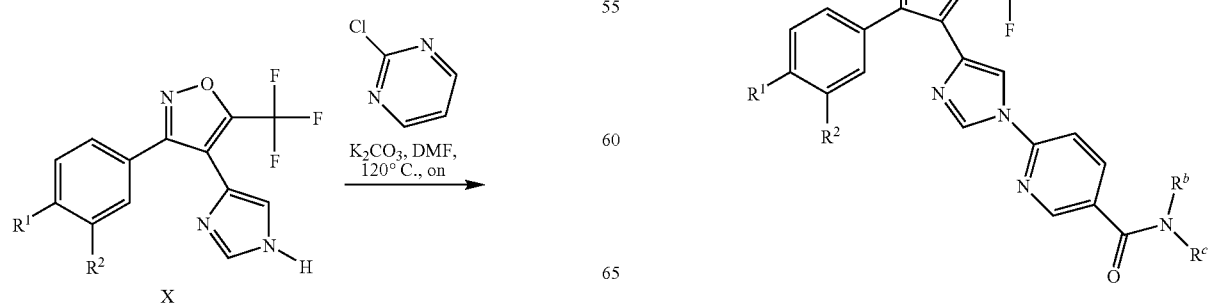

Scheme 8 on = overnight
rt = room temperature
DMF = N,N-dimethylformamide
TBTU = O-(Benzotriazol-1-yl)-N,N,N′,N′-tetramethyluronium tetrafluoroborate
TMEDA = N,N,N′,N′-Tetramethylethylenediamine Hence, present invention provides for a process for the preparation of the compound of formula I comprising the steps of reacting a compound of formula X (a) with a compound of the formula $R^3$—B(OH)$_2$, or (b) with a compound of the formula $R^3$—Y, wherein Y is F or Cl, wherein $R^3$ is phenyl or 6-membered heteroaryl, each of which is optionally substituted with one or more
  halogen,
  $C_{1-7}$-alkyl, optionally substituted with halo, hydroxy or cyano,
  $C_{1-7}$-alkoxy,
  —S(O)$_m$—$C_{1-7}$-alkyl, wherein m is 0, 1 or 2,
  cyano,
  nitro,
  —C(O)$R^a$, wherein $R^a$ is
    $C_{1-7}$-alkyl,
    $C_{1-7}$-alkoxy,
    hydroxy,
    —(CH$_2$)$_n$C$_{3-7}$-cycloalkyl,
    —(CH$_2$)$_n$-(3- to 7-membered heterocycloalkyl), optionally substituted by $C_{1-4}$-alkyl, halo, hydroxy, or oxo,
    —O(CH$_2$)$_n$—C$_{3-7}$-cycloalkyl,
  —NC(O)$C_{1-7}$-alkyl,
  —NC(O)O$C_{1-7}$-alkyl, (c) optionally converting the substituent —C(O)$R^a$, wherein $R^a$ is $C_{1-7}$-alkoxy or hydroxy, into a substituent of $R^3$ represented by
  —C(O)N$R^b R^c$, wherein $R^b$ and $R^c$ are independently
    hydrogen,
    $C_{1-7}$-alkyl,
    —(CH$_2$)$_p$-(3- to 7-membered heterocycloalkyl), optionally substituted by $C_{1-4}$-alkyl, halo, hydroxy, or oxo,
    —(CH$_2$)$_p$-(5- or 6-membered heteroaryl) or —(CH$_2$)$_r$-phenyl, each optionally substituted by halo, $C_{1-4}$-alkyl, $C_{1-7}$-haloalkyl, $C_{1-7}$-alkoxy, cyano or nitro,
    —(CH$_2$)$_q$C$_{3-7}$-cycloalkyl,
    $C_{1-7}$-haloalkyl,
    $C_{1-7}$-alkynyl,
    or $R^b$ and $R^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more $C_{1-4}$-alkyl, halo, hydroxy, or oxo;
n is 0, 1, 2, 3 or 4;
p is 0, 1, 2, 3 or 4;
q is 0, 1, 2, 3 or 4;
r is 0, 1, 2, 3 or 4; and (d) optionally converting the compound into a pharmaceutically acceptable salt.

In a certain embodiment, present invention provides for a process for the preparation of the compound of formula I

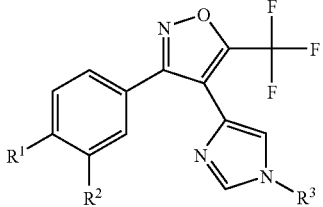

comprising the steps of reacting a compound of formula X

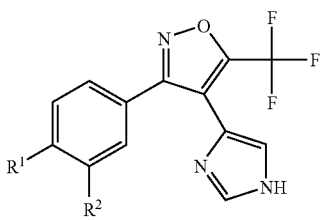

(a) with a compound of the formula $R^3$—$B(OH)_2$, or (b) with a compound of the formula $R^3$—Y, wherein Y is F or Cl, wherein $R^3$ is phenyl or 6-membered heteroaryl, each of which is optionally substituted with one or more
  halogen,
  $C_{1-7}$-alkyl, optionally substituted with halo, hydroxy or cyano,
  $C_{1-7}$-alkoxy,
  cyano,
  nitro,
  —$C(O)R^a$, wherein $R^a$ is
    $C_{1-7}$-alkyl,
    $C_{1-7}$-alkoxy,
    hydroxy, (c) optionally converting the substituent —$C(O)R^a$, wherein $R^a$ is $C_{1-7}$-alkoxy or hydroxy, into a substituent of $R^3$ represented by
  —$C(O)NR^bR^c$, wherein $R^b$ and $R^c$ are independently
    hydrogen,
    3- to 7-membered heterocycloalkyl, optionally substituted by $C_{1-4}$-alkyl, halo, hydroxy, or oxo,
    —$(CH_2)_qC_{3-7}$-cycloalkyl, wherein q is 0 or 1,
    $C_{1-7}$-haloalkyl,
    or $R^b$ and $R^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more $C_{1-4}$-alkyl, halo, hydroxy, or oxo; and (d) optionally converting the compound into a pharmaceutically acceptable salt.

Thereby, the schemes 1-8 describes the processes for preparation of compounds of formula I by the reaction of X with a corresponding electrophilic species, such as boronic acids in the presence of a copper source, for example [Cu(OH).TMEDA]$_2$Cl$_2$ (or other systems previously reported and reviewed in Angew. Chem., 2003, 115, 5558) at ambient temperature. In addition preparation of compounds of formula I is preferably carried out by the reaction of X with a range of arylhalides such as electron deficient arylfluorides, arylchlorides and arylbromides in aprotic polar solvents such as DMF or DMSO at elevated temperatures>100° C. preferably in the presence of a base such a potassium carbonate. Aryl in this context means phenyl or 6-membered heteroaryl as described herein.

As mentioned earlier, the compounds of formula I and their pharmaceutically acceptable salts possess valuable pharmacological properties. It has been found that the compounds of the present invention are ligands for GABA A receptors containing the α5 subunit and are therefore useful in the therapy where cognition enhancement is required.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of $10$-$10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from α5 subunits of the rat GABA A receptor of 100 nM or less. Most preferred are compounds with a Ki (nM)<35. In a preferred embodiment the compounds of the invention are binding selective for the α5 subunit relative to the α1, α2 and α3 subunit.

| Example No. | Ki[nM] hα5 |
| --- | --- |
| 1 | 53.2 |
| 3 | 12.5 |
| 4 | 39.7 |

-continued

| Example No. | Ki[nM] hα5 |
|---|---|
| 5 | 41.2 |
| 7 | 19.7 |
| 8 | 84.2 |
| 9 | 46.1 |
| 10 | 23.6 |
| 11 | 17.6 |
| 12 | 11.7 |
| 13 | 41.2 |
| 17 | 31.5 |
| 23 | 91.1 |
| 27 | 22.1 |
| 28 | 76.7 |
| 29 | 28.4 |
| 31 | 17.1 |
| 35 | 87.4 |
| 36 | 17.2 |
| 37 | 32.3 |
| 39 | 4.9 |
| 40 | 4.1 |
| 43 | 38.2 |
| 47 | 58.6 |
| 51 | 8.5 |
| 54 | 73 |
| 55 | 14.1 |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatin capsules.

EXAMPLE C

Suppositories of the following composition can be manufactured:

|  | mg/supp. |
|---|---|
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size, left to cool, the suppositories then can be removed from the moulds and packed individually in wax paper or metal foil.

The following examples 1-55 are provided for illustration of the invention. They should not be considered as limiting the scope of the invention, but merely as being representative thereof.

EXAMPLE 1

3-Phenyl-4-(1-phenyl-1H-imidazol-4-yl)-5-trifluoromethyl-isoxazole a) 3-Phenyl-5-hydroxy-5-(trifluoromethyl)isoxazoline

Prepared according to *J. Org. Chem.*, 1995, 60, 3907. A solution of benzoyltrifluoroacetone (21 g, 97 mmol) was added dropwise over 1 h, at 20-30° C., to a solution of hydroxylamine HCl (6.82 g, 98 mmol) containing sodium hydroxide (2 N, 51 mL, 102 mmol) and the resulting mixture heated under reflux for 45 min. After cooling to room temperature, the mixture was poured into ice-water (500 mL), the precipitate was filtered off, washed with water and dried under vacuum to afford the title compound (20.51 g, 91%) which was obtained as a white solid. MS: m/e=230.2 [M−H]⁻.

b) 3-Phenyl-4-(1-phenyl-1H-imidazol-4-yl)-5-trifluoromethyl-isoxazole

Prepared according to *J. Org. Chem.*, 1995, 60, 3907. A solution of 3-phenyl-5-hydroxy-5-(trifluoromethyl)isoxazoline (20.4 g, 88 mmol) in trifluoroacetic acid (602 g, 404 mL, 5.3 mol) was heated under reflux for 24 h. After cooling to room temperature, the mixture was added carefully to a sodium carbonate solution (3 N, 880 mL) under ice-bath cooling until the reaction mixture was pH 7. The mixture was then extracted with TBME and the combined organic layers dried over sodium sulfate, filtered and evaporated. The residue was then evaporated and triturated with water to afford the title compound (17.3 g, 92%) which was obtained as a white solid. MS: m/e=214.1 [M+H]⁺.

c) 3-Phenyl-5-trifluoromethyl-isoxazole-4-carboxylic acid

To a solution of 2,2,6,6-tetramethylpiperidine (7.7 g, 9.24 mL, 54 mmol) was in dry THF (62 mL) was added BuLi (1.6 M in hexane, 30.7 mL, 49 mmol) at 0° C. and the resulting mixture stirred at 0° C. for 30 min. Then a solution of 3-phenyl-4-(1-phenyl-1H-imidazol-4-yl)-5-trifluoromethyl-isoxazole (8.72 g, 41 mmol) in dry THF (41 mL) was added dropwise at 0° C. and the resulting mixture stirred at 0° C. for 1 h. The mixture was then quenched with carbon dioxide gas and the resulting mixture stirred at 0° C. for 1 h. The mixture was then poured into HCl (1 N) and the mixture was extracted with ethyl acetate and the combined organic layers dried over sodium sulfate, filtered and evaporated to afford the title compound (10.32 g, 98%) which was obtained as a light brown solid. MS: m/e=256.1 [M−H]⁻.

d) 1-(3-Phenyl-5-trifluoromethyl-isoxazol-4-yl)-ethanone

To a suspension of 3-phenyl-5-trifluoromethyl-isoxazole-4-carboxylic acid (8.92 g, 35 mmol) in toluene (70 mL) was added thionyl chloride (3.8 mL, 52 mmol) and DMF (1 drop) and the resulting mixture heated at 80° C. for 20 h. After cooling to room temperature the mixture was evaporated to give the acid chloride as a dark brown oil (9.65 g). To a solution of magnesium chloride (3.66 g, 39 mmol) in acetonitrile (70 mL) at room temperature was added bis(trimethylsilyl)malonate (9.13 g, 37 mmol) and triethylamine (3.9 g, 5.4 mL, 39 mmol) and after 10 min the mixture was cooled to 0° C. Then a solution of the acid chloride (9.65 g, 35 mmol) in acetonitrile (14 mL) was added dropwise and the resulting mixture stirred at room temperature for 2 h and then HCl (5 N) was added and the mixture heated under reflux for 1 h. After cooling to room temperature, the mixture was poured into water and the mixture was extracted with ethyl acetate and the combined organic layers dried over sodium sulfate, filtered and evaporated. Purification by chromatography (SiO₂, heptane:ethyl acetate=0 to 1:1) afforded the title compound (2.88 g, 32%) which was obtained as a light yellow oil. MS (EI): m/e=255.1 [M]⁺.

Alternatively:

e) 1-(3-Phenyl-5-trifluoromethyl-isoxazol-4-yl)-ethanone

To a solution of 3-phenyl-4-(1-phenyl-1H-imidazol-4-yl)-5-trifluoromethyl-isoxazole (5.0 g, 23 mmol) in 1,2-dimethoxyethane (50 mL) was added BuLi (1.6 M in hexane, 22 mL, 35 mmol) at −78° C. and the resulting mixture stirred for 1 h allowing to warm up to −35° C. and then re-cooled to −78° C. To this mixture was then rapidly added a solution of copper(I) cyanide (2.1 g, 23 mmol) containing lithium chloride (1.99 g, 47 mmol) in dry THF (30 mL) and then allowed to warm up to −35° C. and then this mixture was added to a solution of acetyl chloride (9.2 g, 8.37 mL, 117 mmol) in dry THF (50 mL) at room temperature. After 4 h at room temperature the mixture was diluted with aqueous sodium carbonate and the mixture was extracted with ethyl acetate and the combined organic layers washed with brine, dried over sodium sulfate, filtered and evaporated. Purification by chromatography (SiO₂, heptane:ethyl acetate=100:0 to 4:1) afforded the title compound (4.86 g, 82%) which was obtained as a light yellow oil. MS: m/e 254.2 [M+H]⁺.

f) 2-Bromo-1-(3-phenyl-5-trifluoromethyl-isoxazol-4-yl)-ethanone

To a solution of 1-(3-phenyl-5-trifluoromethyl-isoxazol-4-yl)-ethanone (2.88 g, 11 mmol) in chloroform (11 mL) and AcOH (0.6 mL) at 48° C. was added a solution of bromine (0.61 mL, 12 mmol) in chloroform (3.5 mL) over 5 min keeping the temperature below 50° C. After addition the reaction mixture was allowed to cool down to room temperature and poured into ice-water (200 mL). The layers were separated and the aqueous layer extracted with dichloromethane. The combined organic layers were then washed with water and brine, dried over sodium sulphate and evaporated. Purification by chromatography (SiO₂, heptane:ethyl acetate: 100:0 to 4:1) afforded the title compound (2.2 g, 59%) which was obtained as a light yellow oil. MS: m/e=334.3/336.4 [M+H]⁺.

g) 4-(1H-Imidazol-4-yl)-3-phenyl-5-trifluoromethyl-isoxazole

A suspension of 2-bromo-1-(3-phenyl-5-trifluoromethyl-isoxazol-4-yl)-ethanone (1.71 g, 5 mmol) in formamide (5.52 g, 4.88 mL, 123 mmol) and water (0.5 mL, 3.1 mmol) was heated at 80° C. for 16 h. The resulting mixture was then poured into water (5 mL) and neutralised to pH 7 and then extracted with ethyl acetate. The combined organic extracts were then made basic with sodium carbonate (1 N, 20 mL) and then extracted with ethyl acetate. The combined organic extracts were then dried over sodium sulphate and evaporated. Purification by chromatography (SiO₂, heptane:ethyl acetate=6:4 to 0:100) afforded the title compound (375 mg, 26%) which was obtained as brown oil. MS: m/e=280.1 [M+H]$^+$.

Alternatively (Steps h and i):

h) 4-(3-Phenyl-5-trifluoromethyl-isoxazol-4-yl)-1H-imidazole-2-carboxylic acid methyl ester A solution of 2-bromo-1-(3-phenyl-5-trifluoromethyl-isoxazol-4-yl)-ethanone (300 mg, 0.9 mmol) in DMSO (2 mL) and water (20 mL) was stirred at room temperature for 4 days. The mixture was then evaporated and purified by chromatography (SiO$_2$, heptane:ethyl acetate=100:0 to 0:100) afforded the glyoxal intermediate (116 mg, 45%) as a yellow gum which was then dissolved in acetonitrile (4 mL) and 2-hydroxy-2-methoxyacetic acid methyl ester (140 mg, 1.2 mmol) was added. This mixture was then added to a solution of ammonium acetate (88.6 mg, 1.2 mmol) in acetonitrile (1 mL) containing 2-hydroxy-2-methoxyacetic acid methyl ester (50 mg, 0.4 mmol) at 0° C. over 2 min. The resulting mixture was then stirred at 0° C. for 1 h and warmed up to room temperature over 30 min. The mixture was then extracted with ethyl acetate and the combined organic extracts washed with an aqueous saturated sodium hydrogen carbonate solution, brine, dried over sodium sulfate and evaporated. Purification by chromatography (SiO$_2$, heptane:ethyl acetate=6:4 to 0:100) afforded the title compound (55 mg, 43%) which was obtained as an off-white solid. MS: m/e=338.1 [M+H]$^+$.

i) 4-(1H-Imidazol-4-yl)-3-phenyl-5-trifluoromethyl-isoxazole

To a solution of 4-(3-phenyl-5-trifluoromethyl-isoxazol-4-yl)-1H-imidazole-2-carboxylic acid methyl ester (100 mg, 0.3 mmol) in THF (1 mL) was added a solution of lithium hydroxide monohydrate (24.8 mg, 0.6 mmol) in water (1 mL) and the resulting mixture stirred at room temperature overnight, and then at 50° C. overnight. After cooling to room temperature the mixture was acidified to pH 1 with HCl (25%, 3 drops) and methanol (2 drops) added. The mixture was then heated at 80° C. for 34 h and left at room temperature for 2 days. The mixture was then extracted with ethyl acetate and the combined organic extracts washed with an aqueous saturated sodium hydrogen carbonate solution, brine, dried over sodium sulfate and evaporated to afford the title compound (70 mg, 85%) which was obtained as an off-white solid. MS: m/e 280.1 [M+H]$^+$.

j) 3-Phenyl-4-(1-phenyl-1H-imidazol-4-yl)-5-trifluoromethyl-isoxazole

To a mixture of 4-(1H-imidazol-4-yl)-3-phenyl-5-trifluoromethyl-isoxazole (90 mg, 0.32 mmol) containing [Cu(OH).TMEDA]$_2$Cl$_2$ (14.95 mg, 0.032 mmol) in dry methanol (5 mL) was added phenylboronic acid (81.0 mg, 0.64 mmol) under an air atmosphere and the resulting mixture stirred at room temperature overnight. After this time, the resulting mixture was diluted with water and extracted with ethyl acetate. The organic extracts were then dried over sodium sulphate and evaporated. Purification by chromatography (SiO$_2$, heptane:ethyl acetate=9:1 to 3:2) afforded the title compound (48 mg, 42%) which was obtained as a white solid. MS: m/e 356.3 [M+H]$^+$.

EXAMPLE 2

4-[1-(4-Fluoro-phenyl)-1H-imidazol-4-yl]-3-phenyl-5-trifluoromethyl-isoxazole

As described for Example 1j, 4-(1H-imidazol-4-yl)-3-phenyl-5-trifluoromethyl-isoxazole (100 mg, 0.36 mmol) was converted, using 4-fluorophenylboronic acid instead of phenylboronic acid, to the title compound (70 mg, 52%) which was obtained as a white solid. MS: m/e=374.2 [M+H]$^+$.

EXAMPLE 3

1-{4-[4-(3-Phenyl-5-trifluoromethyl-isoxazol-4-yl)-imidazol-1-yl]-phenyl}-ethanone To a solution of 4-(1H-imidazol-4-yl)-3-phenyl-5-trifluoromethyl-isoxazole (70 mg, 0.25 mmol) in DMF (2.5 mL) was added 4-fluoroacetophenone (35 mg, 0.25 mmol) and potassium carbonate (69.1 mg, 0.5 mmol) and the resulting mixture heated at 120° C. overnight. The resulting mixture was then poured into HCl (1 N, 200 mL) and extracted with ethyl acetate which was then washed with brine, dried over sodium sulphate and evaporated. Purification by preparative HPLC on reversed phase eluting with an acetonitrile/water [0.1% aq NH$_3$ (25%)] gradient afforded the title compound (25 mg, 25%) which was obtained as a white solid. MS: m/e=398.1 [M+H]$^+$.

EXAMPLE 4

3-Phenyl-5-trifluoromethyl-4-[1-(4-trifluoromethyl-phenyl)-1H-imidazol-4-yl]-isoxazole To a solution of 4-(1H-imidazol-4-yl)-3-phenyl-5-trifluoromethyl-isoxazole (69.8 mg, 0.25 mmol) in DMF (1.0 mL) was added 4-fluorobenzotrifluoride (32 µL, 41 mg, 0.25 mmol) and potassium carbonate (69.1 mg, 0.5 mmol) and the resulting mixture heated at 120° C. overnight. The resulting mixture was then poured into water and extracted with ethyl acetate which was then washed with brine, dried over sodium sulphate and evaporated. Purification by chromatography (SiO$_2$, heptane:ethyl acetate=60:40) afforded the title compound (68 mg, 64%) which was obtained as an off-white solid. MS: m/e=424.3 [M+H]$^+$.

EXAMPLE 5

4-[4-(3-Phenyl-5-trifluoromethyl-isoxazol-4-yl)-imidazol-1-yl]-benzonitrile

As described for Example 4, 4-(1H-imidazol-4-yl)-3-phenyl-5-trifluoromethyl-isoxazole (90 mg, 0.32 mmol) was converted, using 4-fluorobenzonitrile instead of 4-fluorobenzotrifluoride, to the title compound (60 mg, 49%) which was obtained as a white solid. MS: m/e=381.2 [M+H]$^+$.

EXAMPLE 6

4-[4-(3-Phenyl-5-trifluoromethyl-isoxazol-4-yl)-imidazol-1-yl]-benzoic acid methyl ester As described for Example 1j, 4-(1H-imidazol-4-yl)-3-phenyl-5-trifluoromethyl-isoxazole (450 mg, 1.6 mmol) was converted, using (4-methoxycarbonylphenyl)boronic acid instead of phenylboronic acid, to the title compound (180 mg, 27%) which was obtained as a colourless oil. MS: m/e=414.3 [M+H]$^+$.

Alternatively: As described for Example 4, 4-(1H-imidazol-4-yl)-3-phenyl-5-trifluoromethyl-isoxazole (450 mg, 0.1.6 mmol) was converted, using methyl 4-fluorobenzene instead of 4-fluorobenzotrifluoride, to the title compound (280 mg, 42%) which was obtained as alight yellow solid. MS: m/e=414.3 [M+H]$^+$.

EXAMPLE 7

4-[1-(4-Nitro-phenyl)-1H-imidazol-4-yl]-3-phenyl-5-trifluoromethyl-isoxazole

As described for Example 3, 4-(1H-imidazol-4-yl)-3-phenyl-5-trifluoromethyl-isoxazole (70 mg, 0.25 mmol) was converted, using 4-fluoronitrobenzene instead of 4-fluoroacetophenone, to the title compound (12 mg, 12%) which was obtained as a yellow solid. MS: m/e=401.0 [M+H]$^+$.

EXAMPLE 8

3-Phenyl-4-(1-p-tolyl-1H-imidazol-4-yl)-5-trifluoromethyl-isoxazole

As described for Example 1j, 4-(1H-imidazol-4-yl)-3-phenyl-5-trifluoromethyl-isoxazole (100 mg, 0.36 mmol) was converted, using p-tolylboronic acid instead of phenylboronic acid, to the title compound (55 mg, 42%) which was obtained as a white solid. MS (ESI): m/e=370.1 [M+H]$^+$.

EXAMPLE 9

4-[1-(4-Methoxy-phenyl)-1H-imidazol-4-yl]-3-phenyl-5-trifluoromethyl-isoxazole

As described for Example 1j, 4-(1H-imidazol-4-yl)-3-phenyl-5-trifluoromethyl-isoxazole (100 mg, 0.36 mmol) was converted, using 4-methoxyphenylboronic acid instead of phenylboronic acid, to the title compound (90 mg, 65%) which was obtained as a white solid. MS (ESI): m/e=386.1 [M+H]$^+$.

EXAMPLE 10

N-Cyclopropylmethyl-4-[4-(3-phenyl-5-trifluoromethyl-isoxazol-4-yl)-imidazol-1-yl]-benzamide A solution of trimethylaluminium (2 M in toluene, 338 μL, 0.68 mmol) and cyclopropanemethylamine (60.4 μL, 0.68 mmol) in dioxane (9 mL) was stirred at room temperature for 1 h and then a solution of 4-[4-(3-phenyl-5-trifluoromethyl-isoxazol-4-yl)-imidazol-1-yl]-benzoic acid methyl ester (70 mg, 0.17 mmol) in dioxane (6 mL) was added. The resulting mixture was then heated at 85-95° C. overnight and then cooled to room temperature and then poured into water and extracted with ethyl acetate which was then washed with brine, dried over sodium sulphate and evaporated. Purification by chromatography (SiO$_2$, heptane:ethyl acetate=60:40) afforded the title compound (60 mg, 78%) which was obtained as a colourless oil. MS: m/e=453.3 [M+H]$^+$.

EXAMPLE 11

4-[4-(3-Phenyl-5-trifluoromethyl-isoxazol-4-yl)-imidazol-1-yl]-N-(2,2,2-trifluoro-ethyl)-benzamide As described for Example 10, 4-[4-(3-phenyl-5-trifluoromethyl-isoxazol-4-yl)-imidazol-1-yl]-benzoic acid methyl ester (70 mg, 0.17 mmol) was converted, using 2,2,2-trifluoroethylamine instead of cyclopropanemethylamine, to the title compound (40 mg, 49%) which was obtained as a white solid. MS: m/e=481.0 [M+H]$^+$.

EXAMPLE 12

N-Cyclopropyl-4-[4-(3-phenyl-5-trifluoromethyl-isoxazol-4-yl)-imidazol-1-yl]-benzamide As described for Example 10, 4-[4-(3-phenyl-5-trifluoromethyl-isoxazol-4-yl)-imidazol-1-yl]-benzoic acid methyl ester (70 mg, 0.17 mmol) was converted, using cyclopropylamine instead of cyclopropanemethylamine, to the title compound (20 mg, 27%) which was obtained as a white solid. MS: m/e=439.2 [M+H]$^+$.

EXAMPLE 13

4-[4-(3-Phenyl-5-trifluoromethyl-isoxazol-4-yl)-imidazol-1-yl]-N-(tetrahydro-pyran-4-yl)-benzamide As described for Example 10, 4-[4-(3-phenyl-5-trifluoromethyl-isoxazol-4-yl)-imidazol-1-yl]-benzoic acid methyl ester (80 mg, 0.19 mmol) was converted, using 4-aminotetrahydropyran instead of cyclopropanemethylamine, to the title compound (75 mg, 80%) which was obtained as a white foam. MS: m/e=483.2 [M+H]$^+$.

EXAMPLE 14

Morpholin-4-yl-{4-[4-(3-phenyl-5-trifluoromethyl-isoxazol-4-yl)-imidazol-1-yl]-phenyl}-methanone As described for Example 10, 4-[4-(3-phenyl-5-trifluoromethyl-isoxazol-4-yl)-imidazol-1-yl]-benzoic acid methyl ester (70 mg, 0.17 mmol) was converted, using morpholine instead of cyclopropanemethylamine, to the title compound (32 mg, 40%) which was obtained as a white foam. MS: m/e=469.1 [M+H]$^+$.

EXAMPLE 15

{4-[4-(3-Phenyl-5-trifluoromethyl-isoxazol-4-yl)-imidazol-1-yl]-phenyl}-thiomorpholin-4-yl-methanone As described for Example 10, 4-[4-(3-phenyl-5-trifluoromethyl-isoxazol-4-yl)-imidazol-1-yl]-benzoic acid methyl ester (70 mg, 0.17 mmol) was converted, using thiomorpholine instead of cyclopropanemethylamine, to the title compound (55 mg, 67%) which was obtained as a light yellow solid. MS: m/e=485.1 [M+H]$^+$.

EXAMPLE 16

2-[4-(3-Phenyl-5-trifluoromethyl-isoxazol-4-yl)-imidazol-1-yl]-5-trifluoromethyl-pyridine As described for Example 4, 4-(1H-imidazol-4-yl)-3-phenyl-5-trifluoromethyl-isoxazole (100 mg, 0.36 mmol) was converted, using 2-fluoro-5-(trifluoromethyl)pyridine instead of 4-fluorobenzotrifluoride, to the title compound (120 mg, 79%) which was obtained as a white solid. MS: m/e=425.0 [M+H]$^+$.

EXAMPLE 17

6-[4-(3-Phenyl-5-trifluoromethyl-isoxazol-4-yl)-imidazol-1-yl]-nicotinic acid methyl ester As described for Example 4, 4-(1H-imidazol-4-yl)-3-phenyl-5-trifluoromethyl-isoxazole (450 mg, 0.1.6 mmol) was converted, using methyl 6-chloronicotinate instead of 4-fluorobenzotrifluoride, to the title compound (510 mg, 76%) which was obtained as a white solid. MS: m/e=415.2 [M+H]$^+$.

EXAMPLE 18

N-Cyclopropylmethyl-6-[4-(3-phenyl-5-trifluoromethyl-isoxazol-4-yl)-imidazol-1-yl]-nicotinamide As described for Example 10, 6-[4-(3-phenyl-5-trifluoromethyl-isoxazol-4-yl)-imidazol-1-yl]-nicotinic acid methyl ester (90 mg, 0.22 mmol), instead of 4-[4-(3-phenyl-5-trifluoromethyl-isoxazol-4-yl)-imidazol-1-yl]-benzoic acid methyl ester was converted, to the title compound (50 mg, 51%) which was obtained as a white solid. MS: m/e=454.2 [M+H]$^+$.

EXAMPLE 19

6-[4-(3-Phenyl-5-trifluoromethyl-isoxazol-4-yl)-imidazol-1-yl]-N-(2,2,2-trifluoro-ethyl)-nicotinamide As described for Example 18, 6-[4-(3-phenyl-5-trifluoromethyl-isoxazol-4-yl)-imidazol-1-yl]-nicotinic acid methyl ester (90 mg, 0.22 mmol), was converted, using 2,2,2-trifluoroethylamine instead of cyclopropanemethylamine, to the title compound (60 mg, 57%) which was obtained as a white solid. MS: m/e=482.1 [M+H]$^+$.

EXAMPLE 20

N-Cyclopropyl-6-[4-(3-phenyl-5-trifluoromethyl-isoxazol-4-yl)-imidazol-1-yl]-nicotinamide As described for Example 18, 6-[4-(3-phenyl-5-trifluoromethyl-isoxazol-4-yl)-imidazol-1-yl]-nicotinic acid methyl ester (90 mg, 0.22 mmol), was converted, using cyclopropylamine instead of cyclopropanemethylamine, to the title compound (50 mg, 52%) which was obtained as a white solid. MS: m/e=440.1 [M+H]$^+$.

EXAMPLE 21

6-[4-(3-Phenyl-5-trifluoromethyl-isoxazol-4-yl)-imidazol-1-yl]-N-(tetrahydro-pyran-4-yl)-nicotinamide As described for Example 18, 6-[4-(3-phenyl-5-trifluoromethyl-isoxazol-4-yl)-imidazol-1-yl]-nicotinic acid methyl ester (100 mg, 0.24 mmol), was converted, using 4-aminotetrahydropyran instead of cyclopropanemethylamine, to the title compound (110 mg, 86%) which was obtained as a white solid. MS: m/e=484.2 [M+H]$^+$.

EXAMPLE 22

Morpholin-4-yl-{6-[4-(3-phenyl-5-trifluoromethyl-isoxazol-4-yl)-imidazol-1-yl]-pyridin-3-yl}-methanone As described for Example 18, 6-[4-(3-phenyl-5-trifluoromethyl-isoxazol-4-yl)-imidazol-1-yl]-nicotinic acid methyl ester (90 mg, 0.22 mmol), was converted, using morpholine instead of cyclopropanemethylamine, to the title compound (28 mg, 28%) which was obtained as a yellow oil. MS: m/e=470.1 [M+H]$^+$.

EXAMPLE 23

{6-[4-(3-Phenyl-5-trifluoromethyl-isoxazol-4-yl)-imidazol-1-yl]-pyridin-3-yl}-thiomorpholin-4-yl-methanone As described for Example 18, 6-[4-(3-phenyl-5-trifluoromethyl-isoxazol-4-yl)-imidazol-1-yl]-nicotinic acid methyl ester (70 mg, 0.17 mmol), was converted, using thiomorpholine instead of cyclopropanemethylamine, to the title compound (42 mg, 51%) which was obtained as a colourless oil. MS: m/e=486.0 [M+H]$^+$.

EXAMPLE 24

1-(4-{4-[3-(4-Fluoro-phenyl)-5-trifluoromethyl-isoxazol-4-yl]-imidazol-1-yl}-phenyl)-ethanone a) 4,4,4-Trifluoro-1-(4-fluoro-phenyl)-butane-1,3-dione To a solution of ethyl trifluoroacetate (23.9 mL, 199 mmol) in TBME (230 mL) containing sodium methoxide (5.4 M, 39.6 mL, 214 mmol) was added 4-fluoroacetophenone (25 g, 181 mmol) and the resulting mixture stirred at room temperature for 3 h and then poured into ice-water. The mixture was then diluted with HCl (2 N, 200 mL) and then extracted with ethyl acetate. The combined organic extracts were then dried over sodium sulfate and evaporated to afford the title compound (40.9 g, 97%) which was obtained as an orange oil. MS: m/e=232.9 [M−H]$^−$.

b) 3-(4-Fluoro-phenyl)-5-trifluoromethyl-4,5-dihydro-isoxazol-5-ol

As described for Example 1a, 4,4,4-trifluoro-1-(4-fluorophenyl)-butane-1,3-dione (12.39 g, 174.7 mmol), instead of benzoyltrifluoroacetone, was converted to the title compound (39.6 g, 92%) which was obtained as a light brown solid. MS: m/e=247.9 [M−H]$^−$.

c) 3-(4-Fluoro-phenyl)-5-trifluoromethyl-isoxazole

As described for Example 1b, 3-(4-fluoro-phenyl)-5-trifluoromethyl-4,5-dihydro-isoxazol-5-ol (35.6 g, 142.9 mmol), instead of 3-phenyl-5-hydroxy-5-(trifluoromethyl) isoxazoline, was converted to the title compound (32.2 g, 98%) which was obtained as a light brown solid. MS: m/e=298.1 [M+H]$^+$.

d) 1-[3-(4-Fluoro-phenyl)-5-trifluoromethyl-isoxazol-4-yl]-ethanone

As described for Example 1e, 3-(4-fluoro-phenyl)-5-trifluoromethyl-isoxazole (50.0 mg, 216 mmol), instead of 3-phenyl-4-(1-phenyl-1H-imidazol-4-yl)-5-trifluoromethyl-isoxazole, was converted to the title compound (50.2 mg, 85%) which was obtained as a light yellow oil. MS: m/e=272.1 $[M-H]^-$.

e) 2-Bromo-1-[3-(4-fluoro-phenyl)-5-trifluoromethyl-isoxazol-4-yl]-ethanone

As described for Example 1f, 1-[3-(4-fluoro-phenyl)-5-trifluoromethyl-isoxazol-4-yl]-ethanone (49.8 mg, 182 mmol), instead of 1-(3-phenyl-5-trifluoromethyl-isoxazol-4-yl)-ethanone, was converted to the title compound (60.2 mg, 94%) which was obtained as a light yellow solid. MS: m/e=350.9/351.9 $[M-H]^-$.

f) 3-(4-Fluoro-phenyl)-4-(1H-imidazol-4-yl)-5-trifluoromethyl-isoxazole

As described for Example 1g, 2-bromo-1-[3-(4-fluoro-phenyl)-5-trifluoromethyl-isoxazol-4-yl]-ethanone (20 g, 57 mmol), instead of 2-bromo-1-(3-phenyl-5-trifluoromethyl-isoxazol-4-yl)-ethanone, was converted to the title compound (3.32 g, 20%) which was obtained as a light brown solid. MS: m/e=298.0 $[M-H]^-$.

g) 1-(4-{4-[3-(4-Fluoro-phenyl)-5-trifluoromethyl-isoxazol-4-yl]-imidazol-1-yl}-phenyl)-ethanone As described for Example 4, 3-(4-fluoro-phenyl)-4-(1H-imidazol-4-yl)-5-trifluoromethyl-isoxazole (100 mg, 0.34 mmol) and 4-fluoroacetophenone, instead of 4-(1H-imidazol-4-yl)-3-phenyl-5-trifluoromethyl-isoxazole and 4-fluorobenzotrifluoride, was converted to the title compound (70 mg, 50%) which was obtained as a white solid. MS: m/e=416.3 $[M+H]^+$.

EXAMPLE 25

3-(4-Fluoro-phenyl)-5-trifluoromethyl-4-[1-(4-trifluoromethyl-phenyl)-1H-imidazol-4-yl]-isoxazole As described for Example 24, 3-(4-fluoro-phenyl)-4-(1H-imidazol-4-yl)-5-trifluoromethyl-isoxazole (100 mg, 0.34 mmol), using 4-fluorobenzotrifluoride instead of 4-fluoroacetophenone, was converted to the title compound (50 mg, 34%) which was obtained as a white solid. MS: m/e=442.1 $[M+H]^+$.

EXAMPLE 26

4-{4-[3-(4-Fluoro-phenyl)-5-trifluoromethyl-isoxazol-4-yl]-imidazol-1-yl}-benzonitrile As described for Example 24, 3-(4-fluoro-phenyl)-4-(1H-imidazol-4-yl)-5-trifluoromethyl-isoxazole (100 mg, 0.34 mmol), using 4-fluorobenzonitrile instead of 4-fluoroacetophenone, was converted to the title compound (90 mg, 67%) which was obtained as a white solid. MS: m/e=399.1 $[M+H]^+$.

EXAMPLE 27

4-{4-[3-(4-Fluoro-phenyl)-5-trifluoromethyl-isoxazol-4-yl]-imidazol-1-yl}-benzoic acid methyl ester As described for Example 24, 3-(4-fluoro-phenyl)-4-(1H-imidazol-4-yl)-5-trifluoromethyl-isoxazole (900 mg, 3.0 mmol), using methyl 4-fluorobenzoate instead of 4-fluoroacetophenone, was converted to the title compound (580 mg, 44%) which was obtained as a white solid. MS: m/e=432.3 $[M+H]^+$.

EXAMPLE 28

4-{4-[3-(4-Fluoro-phenyl)-5-trifluoromethyl-isoxazol-4-yl]-imidazol-1-yl}-benzoic acid As described for Example 24, 3-(4-fluoro-phenyl)-4-(1H-imidazol-4-yl)-5-trifluoromethyl-isoxazole (900 mg, 3.0 mmol), using methyl 4-fluorobenzoate instead of 4-fluoroacetophenone, was converted to the title compound (190 mg, 15%) which was obtained as a white solid. MS: m/e=416.3 $[M+H]^+$.

EXAMPLE 29

2-(4-{4-[3-(4-Fluoro-phenyl)-5-trifluoromethyl-isoxazol-4-yl]-imidazol-1-yl}-phenyl)-propan-2-ol To a solution of 1-(4-{4-[3-(4-fluoro-phenyl)-5-trifluoromethyl-isoxazol-4-yl]-imidazol-1-yl}-phenyl)-ethanone (50 mg, 0.12 mmol) in dry THF (2 mL) was added methylmagnesium bromide (3 M, 44 µL, 0.13 mmol) under nitrogen at room temperature and the resulting mixture stirred for 18 h, after which time methylmagnesium bromide (3 M, 40 µL, 0.12 mmol) was added and the resulting mixture stirred for 19 h. The mixture was then diluted with HCl (0.1 N) and then extracted with ethyl acetate. The combined organic extracts were then dried over sodium sulphate and evaporated. Purification by chromatography ($SiO_2$, heptane:ethyl acetate=1:3 to 0:100) afforded the title compound (25 mg, 48%) which was obtained as a white solid. MS: m/e=432.3 $[M+H]^+$.

EXAMPLE 30

3-(4-Fluoro-phenyl)-4-[1-(4-nitro-phenyl)-1H-imidazol-4-yl]-5-trifluoromethyl-isoxazole As described for Example 24, 3-(4-fluoro-phenyl)-4-(1H-imidazol-4-yl)-5-trifluoromethyl-isoxazole (100 mg, 0.34 mmol), using 1-fluoro-4-nitrobenzene instead of 4-fluoroacetophenone, was converted to the title compound (100 mg, 71%) which was obtained as a yellow solid. MS: m/e=417.1 $[M-H]^-$.

EXAMPLE 31

4-{4-[3-(4-Fluoro-phenyl)-5-trifluoromethyl-isoxazol-4-yl]-imidazol-1-yl}-benzamide To a solution of 4-{4-[3-(4-Fluoro-phenyl)-5-trifluoromethyl-isoxazol-4-yl]-imidazol-1-yl}-benzoic acid (90 mg, 0.22 mmol) in THF (4 mL), was added 1-ethyl-3-(3-dimethylaminopropyl)-carbodiimide HCl (50.7 mg, 0.26 mmol) and N-hydroxybenzotriazole (40.5 mg, 0.0.6 mmol), followed by adding ammonium chloride (40.6 mg, 0.76 mmol) and N,N-diisopropylethylamine (199.2 µL, 1.1 mmol) and the reaction mixture was stirred at room temperature overnight. Then 1-ethyl-3-(3-dimethylaminopropyl)-carbodiimide HCl (50.7 mg, 0.26 mmol) and N-hydroxybenzotriazole (40.5 mg, 0.0.6 mmol), followed by adding ammonium chloride (40.6 mg, 0.76 mmol) and N,N-diisopropylethylamine (199.2 µL, 1.1 mmol) was added and the reaction mixture was stirred at room temperature overnight. The mixture was then extracted with ethyl acetate and the combined organic extracts were then dried over sodium sulphate and evaporated. Purification by chromatography (SiO$_2$, heptane:ethyl acetate=1:3 to 0:100) afforded the title compound (38 mg, 42%) which was obtained as a white solid. MS: m/e=417.4 [M+H]$^+$.

EXAMPLE 32

N-Cyclopropylmethyl-4-{4-[3-(4-fluoro-phenyl)-5-trifluoromethyl-isoxazol-4-yl]-imidazol-1-yl}-benzamide As described for Example 10, 4-{4-[3-(4-fluoro-phenyl)-5-trifluoromethyl-isoxazol-4-yl]-imidazol-1-yl}-benzoic acid methyl ester (100 mg, 0.23 mmol), instead of 4-[4-(3-phenyl-5-trifluoromethyl-isoxazol-4-yl)-imidazol-1-yl]-benzoic acid methyl ester was converted, to the title compound (75 mg, 69%) which was obtained as a white solid. MS: m/e=471.0 [M+H]$^+$.

EXAMPLE 33

4-{4-[3-(4-Fluoro-phenyl)-5-trifluoromethyl-isoxazol-4-yl]-imidazol-1-yl}-N-(2,2,2-trifluoro-ethyl)-benzamide As described for Example 32, 4-{4-[3-(4-fluoro-phenyl)-5-trifluoromethyl-isoxazol-4-yl]-imidazol-1-yl}-benzoic acid methyl ester (100 mg, 0.23 mmol) was converted, using 2,2,2-trifluoroethylamine instead of cyclopropanemethylamine, to the title compound (100 mg, 87%) which was obtained as a white solid. MS: m/e=498.9 [M+H]$^+$.

EXAMPLE 34

N-Cyclopropyl-4-{4-[3-(4-fluoro-phenyl)-5-trifluoromethyl-isoxazol-4-yl]-imidazol-1-yl}-benzamide As described for Example 32, 4-{4-[3-(4-fluoro-phenyl)-5-trifluoromethyl-isoxazol-4-yl]-imidazol-1-yl}-benzoic acid methyl ester (100 mg, 0.23 mmol) was converted, using 2,2,2-trifluoroethylamine instead of cyclopropanemethylamine, to the title compound (70 mg, 66%) which was obtained as a white solid. MS: m/e=457.2 [M+H]$^+$.

EXAMPLE 35

(1,1-Dioxo-1λ6-thiomorpholin-4-yl)-(4-{4-[3-(4-fluoro-phenyl)-5-trifluoromethyl-isoxazol-4-yl]-imidazol-1-yl}-phenyl)-methanone As described for Example 32, 4-{4-[3-(4-fluoro-phenyl)-5-trifluoromethyl-isoxazol-4-yl]-imidazol-1-yl}-benzoic acid methyl ester (100 mg, 0.23 mmol) was converted, using thiomorpholine 1,1-dioxide (125.4 mg, 0.9 mmol) instead of cyclopropanemethylamine, to the title compound (95 mg, 77%) which was obtained as a white solid. MS: m/e=534.8 [M+H]$^+$.

EXAMPLE 36

1-(6-{4-[3-(4-Fluoro-phenyl)-5-trifluoromethyl-isoxazol-4-yl]-imidazol-1-yl}-pyridin-3-yl)-ethanone As described for Example 24, 3-(4-fluoro-phenyl)-4-(1H-imidazol-4-yl)-5-trifluoromethyl-isoxazole (120 mg, 0.4 mmol), using 1-(6-chloro-3-pyridinyl)-1-ethanone instead of 4-fluoroacetophenone, was converted to the title compound (64 mg, 38%) which was obtained as a light yellow solid. MS: m/e=417.2 [M+H]$^+$.

EXAMPLE 37

6-{4-[3-(4-Fluoro-phenyl)-5-trifluoromethyl-isoxazol-4-yl]-imidazol-1-yl}-nicotinonitrile As described for Example 24, 3-(4-fluoro-phenyl)-4-(1H-imidazol-4-yl)-5-trifluoromethyl-isoxazole (150 mg, 0.51 mmol), using 6-chloro-3-pyridinecarbonitrile instead of 4-fluoroacetophenone, was converted to the title compound (149.5 mg, 74%) which was obtained as a white solid. MS: m/e=398.3 [M−H]$^-$.

EXAMPLE 38

N-Cyclopropylmethyl-6-{4-[3-(4-fluoro-phenyl)-5-trifluoromethyl-isoxazol-4-yl]-imidazol-1-yl}-nicotinamide a) 6-{4-[3-(4-Fluoro-phenyl)-5-trifluoromethyl-isoxazol-4-yl]-imidazol-1-yl}-nicotinic acid methyl ester As described for Example 4, 3-(4-fluoro-phenyl)-4-(1H-imidazol-4-yl)-5-trifluoromethyl-isoxazole (700 mg, 2.4 mmol) instead of 4-(1H-imidazol-4-yl)-3-phenyl-5-trifluoromethyl-isoxazole was converted, using methyl 6-chloronicotinate instead of 4-fluorobenzotrifluoride, to the title compound (720 mg, 71%) which was obtained as a white solid. MS: m/e=433.1 [M+H]$^+$.

b) 6-{4-[3-(4-Fluoro-phenyl)-5-trifluoromethyl-isoxazol-4-yl]-imidazol-1-yl}-N-(2,2,2-trifluoro-ethyl)-nicotinamide As described for Example 10, 6-{4-[3-(4-fluoro-phenyl)-5-trifluoromethyl-isoxazol-4-yl]-imidazol-1-yl}-nicotinic acid methyl ester (100 mg, 0.23 mmol), instead of 4-[4-(3-phenyl-5-trifluoromethyl-isoxazol-4-yl)-imidazol-1-yl]-benzoic acid methyl ester was converted, to the title compound (80 mg, 73%) which was obtained as a white solid. MS: m/e=471.9 [M+H]$^+$.

EXAMPLE 39

6-{4-[3-(4-Fluoro-phenyl)-5-trifluoromethyl-isoxazol-4-yl]-imidazol-1-yl}-N-(2,2,2-trifluoro-ethyl)-nicotinamide As described for Example 38b, 6-{4-[3-(4-fluoro-phenyl)-5-trifluoromethyl-isoxazol-4-yl]-imidazol-1-yl}-nicotinic acid methyl ester (100 mg, 0.23 mmol), was converted, using 2,2,2-trifluoroethylamine (74.19 μL, 0.9 mmol) instead of cyclopropanemethylamine, to the title compound (110 mg, 95%) which was obtained as a white solid. MS: m/e=499.8 [M+H]$^+$.

EXAMPLE 40

N-Cyclopropyl-6-{4-[3-(4-fluoro-phenyl)-5-trifluoromethyl-isoxazol-4-yl]-imidazol-1-yl}-nicotinamide As described for Example 38b, 6-{4-[3-(4-fluoro-phenyl)-5-trifluoromethyl-isoxazol-4-yl]-imidazol-1-yl}-nicotinic acid methyl ester (100 mg, 0.23 mmol), was converted, using cyclopropylamine (66.14 μL, 0.9 mmol) instead of cyclopropanemethylamine, to the title compound (40 mg, 38%) which was obtained as a white solid. MS: m/e=458.2 [M+H]$^+$.

EXAMPLE 41

6-{4-[3-(4-Fluoro-phenyl)-5-trifluoromethyl-isoxazol-4-yl]-imidazol-1-yl}-N-(tetrahydro-pyran-4-yl)-nicotinamide As described for Example 38b, 6-{4-[3-(4-fluoro-phenyl)-5-trifluoromethyl-isoxazol-4-yl]-imidazol-1-yl}-nicotinic acid methyl ester (100 mg, 0.23 mmol), was converted, using 4-aminotetrahydropyran (96.35 μL, 0.9 mmol) instead of cyclopropanemethylamine, to the title compound (115 mg, 99%) which was obtained as a white solid. MS: m/e=501.8 [M+H]$^+$.

EXAMPLE 42

(1,1-Dioxo-1λ6-thiomorpholin-4-yl)-(6-{4-[3-(4-fluoro-phenyl)-5-trifluoromethyl-isoxazol-4-yl]-imidazol-1-yl}-pyridin-3-yl)-methanone As described for Example 38b, 6-{4-[3-(4-fluoro-phenyl)-5-trifluoromethyl-isoxazol-4-yl]-imidazol-1-yl}-nicotinic acid methyl ester (100 mg, 0.23 mmol), was converted, using thiomorpholine 1,1-dioxide (124.9 mL, 0.9 mmol) instead of cyclopropanemethylamine, to the title compound (120 mg, 97%) which was obtained as a colourless oil. MS: m/e=535.8 [M+H]$^+$.

EXAMPLE 43

2-(6-{4-[3-(4-Fluoro-phenyl)-5-trifluoromethyl-isoxazol-4-yl]-imidazol-1-yl}-pyridin-3-yl)-propan-2-ol To a solution of 1-(6-{4-[3-(4-fluoro-phenyl)-5-trifluoromethyl-isoxazol-4-yl]-imidazol-1-yl}-pyridin-3-yl)-ethanone (50 mg, 0.12 mmol) in dry THF (2 mL) was added methylmagnesium bromide (3 M, 44 μL, 0.13 mmol) under nitrogen at room temperature and the resulting mixture stirred for 18 h. The mixture was then diluted with HCl (0.1 N) and then extracted with ethyl acetate. The combined organic extracts were then dried over sodium sulphate and evaporated. Purification by chromatography (SiO$_2$, heptane:ethyl acetate=1:3 to 0:100) afforded the title compound (50.3 mg, 97%) which was obtained as a white solid. MS: m/e=433.3 [M+H]$^+$.

EXAMPLE 44

1-(4-{4-[3-(4-Chloro-phenyl)-5-trifluoromethyl-isoxazol-4-yl]-imidazol-1-yl}-phenyl)-ethanone a) 1-(4-Chloro-phenyl)-4,4,4-trifluoro-butane-1,3-dione As described for Example 24a, 4-chloroacetophenone (20.31 mL, 169 mmol), instead of 4-fluoroacetophenone, was converted to the title compound (42.4 g, 100%) which was obtained as a light red solid. MS: m/e=248.9 [M−H]$^-$.

b) 3-(4-Chloro-phenyl)-5-trifluoromethyl-4,5-dihydro-isoxazol-5-ol

As described for Example 1a, 1-(4-chloro-phenyl)-4,4,4-trifluoro-butane-1,3-dione (11.95 g, 168.5 mmol), instead of benzoyltrifluoroacetone, was converted to the title compound (39.6 g, 89%) which was obtained as a white solid. MS: m/e=266.1 [M+H]$^+$.

c) 3-(4-Chloro-phenyl)-5-trifluoromethyl-isoxazole

As described for Example 1b, 3-(4-chloro-phenyl)-5-trifluoromethyl-4,5-dihydro-isoxazol-5-ol (39.6 g, 149 mmol), instead of 3-phenyl-5-hydroxy-5-(trifluoromethyl)isoxazoline, was converted to the title compound (36.0 g, 98%) which was obtained as a light brown oil. MS: m/e=247.3 [M−H]$^-$.

d) 1-[3-(4-Chloro-phenyl)-5-trifluoromethyl-isoxazol-4-yl]-ethanone

As described for Example 1e, 3-(4-chloro-phenyl)-5-trifluoromethyl-isoxazole (36 g, 145.4 mmol), instead of 3-phenyl-4-(1-phenyl-1H-imidazol-4-yl)-5-trifluoromethyl-isoxazole, was converted to the title compound (25.2 g, 60%) which was obtained as a light orange oil. MS: m/e=287.9 [M−H]$^-$.

e) 2-Bromo-1-[3-(4-chloro-phenyl)-5-trifluoromethyl-isoxazol-4-yl]-ethanone

As described for Example 1f, 1-[3-(4-chloro-phenyl)-5-trifluoromethyl-isoxazol-4-yl]-ethanone (29.3 g, 101 mmol), instead of 1-(3-phenyl-5-trifluoromethyl-isoxazol-4-yl)-ethanone, was converted to the title compound (31.15 g, 84%) which was obtained as a light yellow solid. MS: m/e=365.8/367.7 [M−H]$^-$.

f) 3-(4-Chloro-phenyl)-4-(1H-imidazol-4-yl)-5-trifluoromethyl-isoxazole

As described for Example 1g, 2-bromo-1-[3-(4-chloro-phenyl)-5-trifluoromethyl-isoxazol-4-yl]-ethanone (31 g, 84 mmol), instead of 2-bromo-1-(3-phenyl-5-trifluoromethyl-isoxazol-4-yl)-ethanone, was converted to the title compound (2.88 g, 11%) which was obtained as a white solid. MS: m/e=313.9 [M+H]$^+$.

g) 1-(4-{4-[3-(4-Chloro-phenyl)-5-trifluoromethyl-isoxazol-4-yl]-imidazol-1-yl}-phenyl)-ethanone As described for Example 4, 3-(4-chloro-phenyl)-4-(1H-imidazol-4-yl)-5-trifluoromethyl-isoxazole (100 mg, 0.32 mmol) and 4-fluoroacetophenone, instead of 4-(1H-imidazol-4-yl)-3-phenyl-5-trifluoromethyl-isoxazole and 4-fluorobenzotrifluoride, was converted to the title compound (60 mg, 44%) which was obtained as a light brown solid. MS: m/e=432.2 [M+H]$^+$.

EXAMPLE 45

3-(4-Chloro-phenyl)-5-trifluoromethyl-4-[1-(4-trifluoromethyl-phenyl)-1H-imidazol-4-yl]-isoxazole As described for Example 44, 3-(4-chloro-phenyl)-4-(1H-imidazol-4-yl)-5-trifluoromethyl-isoxazole (100 mg, 0.32 mmol), using 4-fluorobenzotrifluoride instead of 4-fluoroacetophenone, was converted to the title compound (50 mg, 34%) which was obtained as a white solid. MS: m/e=458.1 [M+H]$^+$.

EXAMPLE 46

4-{4-[3-(4-Chloro-phenyl)-5-trifluoromethyl-isoxazol-4-yl]-imidazol-1-yl}-benzonitrile As described for Example 44, 3-(4-chloro-phenyl)-4-(1H-imidazol-4-yl)-5-trifluoromethyl-isoxazole (100 mg, 0.32 mmol), using 4-fluorobenzonitrile instead of 4-fluoroacetophenone, was converted to the title compound (70 mg, 53%) which was obtained as a white solid. MS: m/e=415.2 $[M+H]^+$.

EXAMPLE 47

3-(4-Chloro-phenyl)-4-[1-(4-nitro-phenyl)-1H-imidazol-4-yl]-5-trifluoromethyl-isoxazole As described for Example 44, 3-(4-chloro-phenyl)-4-(1H-imidazol-4-yl)-5-trifluoromethyl-isoxazole (100 mg, 0.32 mmol), using 1-fluoro-4-nitrobenzene instead of 4-fluoroacetophenone, was converted to the title compound (105 mg, 76%) which was obtained as a yellow solid. MS: m/e=492.9 $[M+OAc]^+$.

EXAMPLE 48

6-{4-[3-(4-Chloro-phenyl)-5-trifluoromethyl-isoxazol-4-yl]-imidazol-1-yl}-N-cyclopropylmethyl-nicotinamide a) 6-{4-[3-(4-Chloro-phenyl)-5-trifluoromethyl-isoxazol-4-yl]-imidazol-1-yl}-nicotinic acid methyl ester As described for Example 4, 3-(4-chloro-phenyl)-4-(1H-imidazol-4-yl)-5-trifluoromethyl-isoxazole (700 mg, 2.2 mmol) instead of 4-(1H-imidazol-4-yl)-3-phenyl-5-trifluoromethyl-isoxazole was converted, using methyl 6-chloronicotinate instead of 4-fluorobenzotrifluoride, to the title compound (750 mg, 75%) which was obtained as a white solid. MS: m/e=449.0 $[M+H]^+$.

b) 6-{4-[3-(4-Chloro-phenyl)-5-trifluoromethyl-isoxazol-4-yl]-imidazol-1-yl}-N-cyclopropylmethyl-nicotinamide As described for Example 10, 6-{4-[3-(4-chloro-phenyl)-5-trifluoromethyl-isoxazol-4-yl]-imidazol-1-yl}-nicotinic acid methyl ester (100 mg, 0.23 mmol), instead of 4-[4-(3-phenyl-5-trifluoromethyl-isoxazol-4-yl)-imidazol-1-yl]-benzoic acid methyl ester was converted, to the title compound (90 mg, 83%) which was obtained as a white solid. MS: m/e=488.1 $[M+H]^+$.

EXAMPLE 49

6-{4-[3-(4-Chloro-phenyl)-5-trifluoromethyl-isoxazol-4-yl]-imidazol-1-yl}-N-(2,2,2-trifluoro-ethyl)-nicotinamide As described for Example 48b, 6-{4-[3-(4-chloro-phenyl)-5-trifluoromethyl-isoxazol-4-yl]-imidazol-1-yl}-nicotinic acid methyl ester (100 mg, 0.23 mmol), was converted, using 2,2,2-trifluoroethylamine instead of cyclopropanemethylamine, to the title compound (110 mg, 96%) which was obtained as a white solid. MS: m/e 516.2 $[M+H]^+$.

EXAMPLE 50

6-{4-[3-(4-Chloro-phenyl)-5-trifluoromethyl-isoxazol-4-yl]-imidazol-1-yl}-N-cyclopropyl-nicotinamide As described for Example 48b, 6-{4-[3-(4-chloro-phenyl)-5-trifluoromethyl-isoxazol-4-yl]-imidazol-1-yl}-nicotinic acid methyl ester (100 mg, 0.23 mmol), was converted, using cyclopropylamine instead of cyclopropanemethylamine, to the title compound (80 mg, 76%) which was obtained as a white solid. MS: m/e=474.1 $[M+H]^+$.

EXAMPLE 51

6-{4-[3-(4-Chloro-phenyl)-5-trifluoromethyl-isoxazol-4-yl]-imidazol-1-yl}-N-(tetrahydro-pyran-4-yl)-nicotinamide As described for Example 48b, 6-{4-[3-(4-chloro-phenyl)-5-trifluoromethyl-isoxazol-4-yl]-imidazol-1-yl}-nicotinic acid methyl ester (100 mg, 0.23 mmol), was converted, using 4-aminotetrahydropyran instead of cyclopropanemethylamine, to the title compound (90 mg, 78%) which was obtained as a light yellow solid. MS: m/e=516.4 $[M-H]^-$.

EXAMPLE 52

(6-{4-[3-(4-Chloro-phenyl)-5-trifluoromethyl-isoxazol-4-yl]-imidazol-1-yl}-pyridin-3-yl)-(1,1-dioxo-1λ6-thiomorpholin-4-yl)-methanone As described for Example 48b, 6-{4-[3-(4-chloro-phenyl)-5-trifluoromethyl-isoxazol-4-yl]-imidazol-1-yl}-nicotinic acid methyl ester (100 mg, 0.23 mmol), was converted, using 4-aminotetrahydropyran instead of cyclopropanemethylamine, to the title compound (120 mg, 98%) which was obtained as a light yellow foam. MS: m/e=550.4 $[M-H]^-$.

EXAMPLE 53

N-Cyclopropyl-6-{4-[3-(3-fluoro-phenyl)-5-trifluoromethyl-isoxazol-4-yl]-imidazol-1-yl}-nicotinamide a) 4,4,4-Trifluoro-1-(3-fluoro-phenyl)-butane-1,3-dione As described for Example 24a, 3-fluoroacetophenone (126.1 g, 879 mmol), instead of 4-fluoroacetophenone, was converted to the title compound (186.2 g, 100%) which was obtained as a light red solid. MS: m/e=232.9 $[M-H]^-$.

b) 3-(3-Fluoro-phenyl)-5-trifluoromethyl-4,5-dihydro-isoxazol-5-ol

As described for Example 1a,4,4,4-trifluoro-1-(3-fluoro-phenyl)-butane-1,3-dione (111.8 g, 448 mmol), instead of benzoyltrifluoroacetone, was converted to the title compound (119.0 g, 100%) which was obtained as a white solid. MS: m/e=250.3 $[M+H]^+$.

c) 3-(3-Fluoro-phenyl)-5-trifluoromethyl-isoxazole

As described for Example 1b, 3-(3-fluoro-phenyl)-5-trifluoromethyl-4,5-dihydro-isoxazol-5-ol (60 g, 241 mmol), instead of 3-phenyl-5-hydroxy-5-(trifluoromethyl)isoxazoline, was converted to the title compound (47.5 g, 85%) which was obtained as a light brown solid. MS: m/e=231.1 [M]⁺.

d) 1-[3-(3-Fluoro-phenyl)-5-trifluoromethyl-isoxazol-4-yl]-ethanone

As described for Example 1e, 3-(3-fluoro-phenyl)-5-trifluoromethyl-isoxazole (20 g, 86.5 mmol), instead of 3-phenyl-4-(1-phenyl-1H-imidazol-4-yl)-5-trifluoromethyl-isoxazole, was converted to the title compound (12.2 g, 51%) which was obtained as a light yellow oil. MS: m/e=272.1 [M−H]⁻.

e) 2-Bromo-1-[3-(3-fluoro-phenyl)-5-trifluoromethyl-isoxazol-4-yl]-ethanone

As described for Example 1f, 1-[3-(3-fluoro-phenyl)-5-trifluoromethyl-isoxazol-4-yl]-ethanone (12.2 g, 44.5 mmol), instead of 1-(3-phenyl-5-trifluoromethyl-isoxazol-4-yl)-ethanone, was converted to the title compound (7.2 g, 46%) which was obtained as a light yellow oil. MS: m/e=350.2/352.2 [M−H]⁻.

f) 3-(3-Fluoro-phenyl)-4-(1H-imidazol-4-yl)-5-trifluoromethyl-isoxazole

As described for Example 1g, 2-bromo-1-[3-(3-fluoro-phenyl)-5-trifluoromethyl-isoxazol-4-yl]-ethanone (7.2 g, 20.3 mmol), instead of 2-bromo-1-(3-phenyl-5-trifluoromethyl-isoxazol-4-yl)-ethanone, was converted to the title compound (1.0 g, 17%) which was obtained as a brown solid. MS: m/e=298.3 [M+H]⁺.

g) 6-{4-[3-(3-Fluoro-phenyl)-5-trifluoromethyl-isoxazol-4-yl]-imidazol-1-yl}-nicotinic acid methyl ester As described for Example 4, 3-(3-fluoro-phenyl)-4-(1H-imidazol-4-yl)-5-trifluoromethyl-isoxazole (500 mg, 1.68 mmol) instead of 4-(1H-imidazol-4-yl)-3-phenyl-5-trifluoromethyl-isoxazole was converted, using methyl 6-chloronicotinate instead of 4-fluorobenzotrifluoride, to the title compound (495 mg, 68%) which was obtained as a white solid. MS: m/e=433.3 [M+H]⁺.

h) N-Cyclopropyl-6-{4-[3-(3-fluoro-phenyl)-5-trifluoromethyl-isoxazol-4-yl]-imidazol-1-yl}-nicotinamide As described for Example 12, 6-{4-[3-(3-fluoro-phenyl)-5-trifluoromethyl-isoxazol-4-yl]-imidazol-1-yl}-nicotinic acid methyl ester (80.8 mg, 1.4 mmol), instead of 4-[4-(3-phenyl-5-trifluoromethyl-isoxazol-4-yl)-imidazol-1-yl]-benzoic acid methyl ester was converted, to the title compound (118 mg, 75%) which was obtained as a white solid. MS: m/e=458.3 [M+H]⁺.

EXAMPLE 54

2-[4-(3-Phenyl-5-trifluoromethyl-isoxazol-4-yl)-imidazol-1-yl]-pyrimidine

As described for Example 4, 4-(1H-imidazol-4-yl)-3-phenyl-5-trifluoromethyl-isoxazole (67.4 mg, 0.48 mmol) was converted, using 2-chloropyrimidine instead of 4-fluorobenzotrifluoride, to the title compound (40 mg, 35%) which was obtained as a white solid. MS: m/e=358.2 [M+H]⁺.

EXAMPLE 55

5-[4-(3-Phenyl-5-trifluoromethyl-isoxazol-4-yl)-imidazol-1-yl]-pyrazine-2-carboxylic acid cyclopropylamide To a solution of 4-(1H-imidazol-4-yl)-3-phenyl-5-trifluoromethyl-isoxazole (196 mg, 0.7 mmol) in DMF (1.0 mL) was added methyl 5-chloropyrazine-2-carboxylate (157 mg, 0.9 mmol) and potassium carbonate (194 mg, 1.4 mmol) and the resulting mixture heated at 120° C. overnight. After cooling to room temperature, sodium hydroxide (1 N, 2.1 mL) was added and after 1 h at room temperature the mixture was heated at 60° C. for 1 h. After cooling to room temperature, sodium carbonate (2 N, 10 mL) was added and the mixture extracted with TBME. The aqueous phase was acidified to pH 3 with citric acid and HCl (& N, 3 drops) and extracted with ethyl acetate. The combined organic extracts were then washed with brine, dried over sodium sulphate and evaporated to give the intermediate acid 5-[4-(3-phenyl-5-trifluoromethyl-isoxazol-4-yl)-imidazol-1-yl]-pyrazine-2-carboxylic acid cyclopropylamide (95 mg, 34%) as a brown solid. Then to a solution of 5-[4-(3-phenyl-5-trifluoromethyl-isoxazol-4-yl)-imidazol-1-yl]-pyrazine-2-carboxylic acid cyclopropylamide (90 mg, 0.22 mmol) in DMF (2 mL) was added TBTU (79 mg, 0.25 mmol) and N,N-diisopropylethylamine (145 mg, 190 μL, 1.1 mmol). After stirring at room temperature for 15 min, cyclopropylamine (15 mg, 20 μL, 0.26 mmol) was added. After 18 h, the mixture was diluted with ethyl acetate and washed with sodium carbonate (2 N) and water, and brine, dried over sodium sulphate and evaporated. Purification by chromatography (SiO₂, heptane:ethyl acetate=60:40) afforded the title compound (20 mg, 20%) which was obtained as an off-white solid. MS: m/e=441.2 [M+H]⁺.

The invention claimed is:

1. A compound of formula I

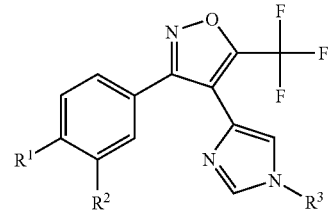

I wherein
  R¹ and R² are each independently hydrogen, halogen, or C₁₋₇-haloalkoxy;
  R³ is phenyl or 6-membered heteroaryl, each of which is optionally substituted by one or more
    halogen,
    C₁₋₇-alkyl, optionally substituted with halo, hydroxy or cyano,
    C₁₋₇-alkoxy,
    —S(O)ₘ—C₁₋₇-alkyl, wherein m is 0, 1 or 2,
    cyano,
    nitro,
    —C(O)Rᵃ, wherein Rᵃ is
      C₁₋₇-alkyl,
      C₁₋₇-alkoxy,
      hydroxy,
      —(CH₂)ₙ—C₃₋₇-cycloalkyl,
      —(CH₂)ₙ-(3- to 7-membered heterocycloalkyl), optionally substituted by C₁₋₄-alkyl, halo, hydroxy, or oxo,
    —O(CH₂)ₙ—C₃₋₇-cycloalkyl,
    —NC(O)C₁₋₇-alkyl, —NC(O)OC$_{1-7}$-alkyl,
—C(O)NR$^b$R$^c$, wherein R$^b$ and R$^c$ are each independently
hydrogen,
C$_{1-7}$-alkyl,
—(CH$_2$)$_p$-(3- to 7-membered heterocycloalkyl), optionally substituted by C$_{1-4}$-alkyl, halo, hydroxy, or oxo,
—(CH$_2$)$_p$-(5- or 6-membered heteroaryl) or —(CH$_2$)$_r$-phenyl, each optionally substituted by halo, C$_{1-4}$-alkyl, C$_{1-7}$-haloalkyl, C$_{1-7}$-alkoxy, cyano or nitro,
—(CH$_2$)$_q$—C$_{3-7}$-cycloalkyl,
C$_{1-7}$-haloalkyl,
C$_{1-7}$-alkynyl,
or R$^b$ and R$^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more C$_{1-4}$-alkyl, halo, hydroxy, or oxo;
n is 0, 1, 2, 3 or 4;
p is 0, 1, 2, 3 or 4;
q is 0, 1, 2, 3 or 4; and
r is 0, 1, 2, 3 or 4;
or a pharmaceutically acceptable salt thereof.

2. The compound of claim 1, wherein R$^1$ and R$^2$ are each independently hydrogen or halogen.

3. The compound of claim 1, wherein R$^3$ is phenyl or 6-membered heteroaryl, each of which is optionally substituted by one or more
halogen,
C$_{1-7}$-alkyl, optionally substituted with halo, hydroxy or cyano,
C$_{1-7}$-alkoxy,
cyano,
nitro,
—C(O)R$^a$, wherein R$^a$ is
C$_{1-7}$-alkyl,
C$_{1-7}$-alkoxy,
hydroxy,
—C(O)NR$^b$R$^c$, wherein R$^b$ and R$^c$ are independently
hydrogen,
3- to 7-membered heterocycloalkyl, optionally substituted by C$_{1-4}$-alkyl, halo, hydroxy, or oxo,
—(CH$_2$)$_q$—C$_{3-7}$-cycloalkyl, wherein q is 0, 1, 2, 3 or 4,
C$_{1-7}$-haloalkyl,
or R$^b$ and R$^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more C$_{1-4}$-alkyl, halo, hydroxy, or oxo.

4. The compound of claim 1, wherein R$^3$ is optionally substituted phenyl.

5. The compound of claim 4, selected from the group consisting of
3-phenyl-4-(1-phenyl-1H-imidazol-4-yl)-5-trifluoromethyl-isoxazole,
4-[1-(4-fluoro-phenyl)-1H-imidazol-4-yl]-3-phenyl-5-trifluoromethyl-isoxazole,
1-{4-[4-(3-phenyl-5-trifluoromethyl-isoxazol-4-yl)-imidazol-1-yl]-phenyl}-ethanone,
3-phenyl-5-trifluoromethyl-4-[1-(4-trifluoromethyl-phenyl)-1H-imidazol-4-yl]-isoxazole,
4-[4-(3-phenyl-5-trifluoromethyl-isoxazol-4-yl)-imidazol-1-yl]-benzonitrile,
4-[4-(3-phenyl-5-trifluoromethyl-isoxazol-4-yl)-imidazol-1-yl]-benzoic acid methyl ester,
4-[1-(4-nitro-phenyl)-1H-imidazol-4-yl]-3-phenyl-5-trifluoromethyl-isoxazole,
3-phenyl-4-(1-p-tolyl-1H-imidazol-4-yl)-5-trifluoromethyl-isoxazole,
4-[1-(4-methoxy-phenyl)-1H-imidazol-4-yl]-3-phenyl-5-trifluoromethyl-isoxazole, and
N-cyclopropylmethyl-4-[4-(3-phenyl-5-trifluoromethyl-isoxazol-4-yl)-imidazol-1-yl]-benzamide.

6. The compound of claim 4, selected from the group consisting of
4-[4-(3-phenyl-5-trifluoromethyl-isoxazol-4-yl)-imidazol-1-yl]-N-(2,2,2-trifluoro-ethyl)-benzamide,
N-cyclopropyl-4-[4-(3-phenyl-5-trifluoromethyl-isoxazol-4-yl)-imidazol-1-yl]-benzamide,
4-[4-(3-phenyl-5-trifluoromethyl-isoxazol-4-yl)-imidazol-1-yl]-N-(tetrahydro-pyran-4-yl)-benzamide,
morpholin-4-yl-{4-[4-(3-phenyl-5-trifluoromethyl-isoxazol-4-yl)-imidazol-1-yl]-phenyl}-methanone,
{4-[4-(3-phenyl-5-trifluoromethyl-isoxazol-4-yl)-imidazol-1-yl]-phenyl}-thiomorpholin-4-yl-methanone,
1-(4-{4-[3-(4-fluoro-phenyl)-5-trifluoromethyl-isoxazol-4-yl]-imidazol-1-yl}-phenyl)-ethanone,
3-(4-fluoro-phenyl)-5-trifluoromethyl-4-[1-(4-trifluoromethyl-phenyl)-1H-imidazol-4-yl]-isoxazole,
4-{4-[3-(4-fluoro-phenyl)-5-trifluoromethyl-isoxazol-4-yl]-imidazol-1-yl}-benzonitrile,
4-{4-[3-(4-fluoro-phenyl)-5-trifluoromethyl-isoxazol-4-yl]-imidazol-1-yl}-benzoic acid methyl ester, and
4-{4-[3-(4-fluoro-phenyl)-5-trifluoromethyl-isoxazol-4-yl]-imidazol-1-yl}-benzoic acid.

7. The compound of claim 4, selected from the group consisting of
2-(4-{4-[3-(4-fluoro-phenyl)-5-trifluoromethyl-isoxazol-4-yl]-imidazol-1-yl}-phenyl)-propan-2-ol,
3-(4-fluoro-phenyl)-4-[1-(4-nitro-phenyl)-1H-imidazol-4-yl]-5-trifluoromethyl-isoxazole,
4-{4-[3-(4-fluoro-phenyl)-5-trifluoromethyl-isoxazol-4-yl]-imidazol-1-yl}-benzamide,
N-cyclopropylmethyl-4-{4-[3-(4-fluoro-phenyl)-5-trifluoromethyl-isoxazol-4-yl]-imidazol-1-yl}-benzamide,
4-{4-[3-(4-fluoro-phenyl)-5-trifluoromethyl-isoxazol-4-yl]-imidazol-1-yl}-N-(2,2,2-trifluoro-ethyl)-benzamide,
N-cyclopropyl-4-{4-[3-(4-fluoro-phenyl)-5-trifluoromethyl-isoxazol-4-yl]-imidazol-1-yl}-benzamide,
(1,1-dioxo-1λ6-thiomorpholin-4-yl)-(4-{4-[3-(4-fluoro-phenyl)-5-trifluoromethyl-isoxazol-4-yl]-imidazol-1-yl}-phenyl)-methanone,
1-(4-{4-[3-(4-chloro-phenyl)-5-trifluoromethyl-isoxazol-4-yl]-imidazol-1-yl}-phenyl)-ethanone,
3-(4-chloro-phenyl)-5-trifluoromethyl-4-[1-(4-trifluoromethyl-phenyl)-1H-imidazol-4-yl]-isoxazole,
4-{4-[3-(4-chloro-phenyl)-5-trifluoromethyl-isoxazol-4-yl]-imidazol-1-yl}-benzonitrile, and
3-(4-chloro-phenyl)-4-[1-(4-nitro-phenyl)-1H-imidazol-4-yl]-5-trifluoromethyl-isoxazole.

8. The compound of claim 1, wherein R$^3$ is optionally substituted pyridinyl.

9. The compound of claim 8, selected from the group consisting of
2-[4-(3-phenyl-5-trifluoromethyl-isoxazol-4-yl)-imidazol-1-yl]-5-trifluoromethyl-pyridine, 6-[4-(3-phenyl-5-trifluoromethyl-isoxazol-4-yl)-imidazol-1-yl]-nicotinic acid methyl ester,
N-cyclopropylmethyl-6-[4-(3-phenyl-5-trifluoromethyl-isoxazol-4-yl)-imidazol-1-yl]-nicotinamide,
6-[4-(3-phenyl-5-trifluoromethyl-isoxazol-4-yl)-imidazol-1-yl]-N-(2,2,2-trifluoro-ethyl)-nicotinamide,
N-cyclopropyl-6-[4-(3-phenyl-5-trifluoromethyl-isoxazol-4-yl)-imidazol-1-yl]-nicotinamide,
6-[4-(3-phenyl-5-trifluoromethyl-isoxazol-4-yl)-imidazol-1-yl]-N-(tetrahydro-pyran-4-yl)-nicotinamide,
morpholin-4-yl-{6-[4-(3-phenyl-5-trifluoromethyl-isoxazol-4-yl)-imidazol-1-yl]-pyridin-3-yl}-methanone,
{6-[4-(3-phenyl-5-trifluoromethyl-isoxazol-4-yl)-imidazol-1-yl]-pyridin-3-yl}-thiomorpholin-4-yl-methanone,
1-(6-{4-[3-(4-fluoro-phenyl)-5-trifluoromethyl-isoxazol-4-yl]-imidazol-1-yl}-pyridin-3-yl)-ethanone,
6-{4-[3-(4-fluoro-phenyl)-5-trifluoromethyl-isoxazol-4-yl]-imidazol-1-yl}-nicotinonitrile, and
N-cyclopropylmethyl-6-{4-[3-(4-fluoro-phenyl)-5-trifluoromethyl-isoxazol-4-yl]-imidazol-1-yl}-nicotinamide.

10. The compound of claim 8, selected from the group consisting of
6-{4-[3-(4-fluoro-phenyl)-5-trifluoromethyl-isoxazol-4-yl]-imidazol-1-yl}-N-(2,2,2-trifluoro-ethyl)-nicotinamide,
N-cyclopropyl-6-{4-[3-(4-fluoro-phenyl)-5-trifluoromethyl-isoxazol-4-yl]-imidazol-1-yl}-nicotinamide,
6-{4-[3-(4-fluoro-phenyl)-5-trifluoromethyl-isoxazol-4-yl]-imidazol-1-yl}-N-(tetrahydro-pyran-4-yl)-nicotinamide,
(1,1-dioxo-1λ6-thiomorpholin-4-yl)-(6-{4-[3-(4-fluoro-phenyl)-5-trifluoromethyl-isoxazol-4-yl]-imidazol-1-yl}-pyridin-3-yl)-methanone,
2-(6-{4-[3-(4-fluoro-phenyl)-5-trifluoromethyl-isoxazol-4-yl]-imidazol-1-yl}-pyridin-3-yl)-propan-2-ol,
6-{4-[3-(4-chloro-phenyl)-5-trifluoromethyl-isoxazol-4-yl]-imidazol-1-yl}-N-cyclopropylmethyl-nicotinamide,
6-{4-[3-(4-chloro-phenyl)-5-trifluoromethyl-isoxazol-4-yl]-imidazol-1-yl}-N-(2,2,2-trifluoro-ethyl)-nicotinamide,
6-{4-[3-(4-chloro-phenyl)-5-trifluoromethyl-isoxazol-4-yl]-imidazol-1-yl}-N-cyclopropyl-nicotinamide,
6-{4-[3-(4-chloro-phenyl)-5-trifluoromethyl-isoxazol-4-yl]-imidazol-1-yl}-N-(tetrahydro-pyran-4-yl)-nicotinamide,
(6-{4-[3-(4-chloro-phenyl)-5-trifluoromethyl-isoxazol-4-yl]-imidazol-1-yl}-pyridin-3-yl)-(1,1-dioxo-1λ6-thiomorpholin-4-yl)-methanone, and
N-cyclopropyl-6-{4-[3-(3-fluoro-phenyl)-5-trifluoromethyl-isoxazol-4-yl]-imidazol-1-yl}-nicotinamide.

11. The compound of claim 1, wherein $R^3$ is substituted pyrazinyl.

12. The compound of claim 11, which is
5-[4-(3-phenyl-5-trifluoromethyl-isoxazol-4-yl)-imidazol-1-yl]-pyrazine-2-carboxylic acid cyclopropylamide.

13. The compound of claim 1, wherein $R^3$ is pyrimidinyl.

14. The compound of claim 13, which is
2-[4-(3-phenyl-5-trifluoromethyl-isoxazol-4-yl)-imidazol-1-yl]-pyrimidine.

15. A pharmaceutical composition comprising a therapeutically effective amount of a compound of formula I

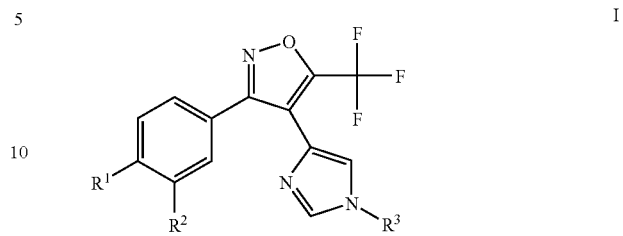

wherein
$R^1$ and $R^2$ are each independently hydrogen, halogen, or $C_{1-7}$-haloalkoxy;
$R^3$ is phenyl or 6-membered heteroaryl, each of which is optionally substituted by one or more
halogen,
$C_{1-7}$-alkyl, optionally substituted with halo, hydroxy or cyano,
$C_{1-7}$-alkoxy,
—$S(O)_m$—$C_{1-7}$-alkyl, wherein m is 0, 1 or 2,
cyano,
nitro,
—$C(O)R^a$, wherein $R^a$ is
$C_{1-7}$-alkyl,
$C_{1-7}$-alkoxy,
hydroxy,
—$(CH_2)_n$—$C_{3-7}$-cycloalkyl,
—$(CH_2)_n$-(3- to 7-membered heterocycloalkyl), optionally substituted by $C_{1-4}$-alkyl, halo, hydroxy, or oxo,
—$O(CH_2)_n$—$C_{3-7}$-cycloalkyl,
—$NC(O)C_{1-7}$-alkyl,
—$NC(O)OC_{1-7}$-alkyl,
—$C(O)NR^bR^c$, wherein $R^b$ and $R^c$ are each independently
hydrogen,
$C_{1-7}$-alkyl,
—$(CH_2)_p$-(3- to 7-membered heterocycloalkyl), optionally substituted by $C_{1-4}$-alkyl, halo, hydroxy, or oxo,
—$(CH_2)_p$-(5- or 6-membered heteroaryl) or —$(CH_2)_r$-phenyl, each optionally substituted by halo, $C_{1-4}$-alkyl, $C_{1-7}$-haloalkyl, $C_{1-7}$-alkoxy, cyano or nitro,
—$(CH_2)_q$—$C_{3-7}$-cycloalkyl,
$C_{1-7}$-haloalkyl,
$C_{1-7}$-alkynyl,
or $R^b$ and $R^c$ together with the nitrogen to which they are bound form a 5- to 7-membered heterocycloalkyl, optionally containing one additional ring heteroatom selected from nitrogen, oxygen and sulfur, wherein the 5- to 7-membered heterocycloalkyl is optionally substituted by one or more $C_{1-4}$-alkyl, halo, hydroxy, or oxo;
n is 0, 1, 2, 3 or 4;
p is 0, 1, 2, 3 or 4;
q is 0, 1, 2, 3 or 4; and
r is 0, 1, 2, 3 or 4;
or a pharmaceutically acceptable salt thereof and a pharmaceutically acceptable carrier.

* * * * *